(12) United States Patent
Sumida et al.

(10) Patent No.: US 9,487,758 B2
(45) Date of Patent: Nov. 8, 2016

(54) GLUCOSE DEHYDROGENASE

(71) Applicant: TOYOBO CO., LTD., Osaka-shi, Osaka (JP)

(72) Inventors: Yosuke Sumida, Tsuruga (JP); Hiroshi Aiba, Tsuruga (JP); Hiroshi Kawaminami, Tsuruga (JP); Rie Hirao, Tsuruga (JP); Yuu Utashima, Tsuruga (JP); Takahide Kishimoto, Tsuruga (JP); Shusaku Yanagidani, Tsuruga (JP)

(73) Assignee: Toyobo Co., Ltd., Osaka (JP)

( * ) Notice: Subject to any disclaimer, the term of this patent is extended or adjusted under 35 U.S.C. 154(b) by 0 days.

(21) Appl. No.: 14/176,701

(22) Filed: Feb. 10, 2014

(65) Prior Publication Data
US 2014/0154777 A1   Jun. 5, 2014

Related U.S. Application Data

(63) Continuation-in-part of application No. PCT/JP2012/070385, filed on Aug. 9, 2012.

(30) Foreign Application Priority Data

Aug. 11, 2011 (JP) ................. 2011-175705
Oct. 6, 2011 (JP) ................. 2011-222269
Oct. 6, 2011 (JP) ................. 2011-222274

(51) Int. Cl.
*C12Q 1/54* (2006.01)
*C12Q 1/32* (2006.01)
*C12N 9/04* (2006.01)

(52) U.S. Cl.
CPC ............... *C12N 9/0006* (2013.01); *C12Q 1/54* (2013.01); *C12Y 101/05* (2013.01)

(58) Field of Classification Search
USPC ............ 435/14, 155, 189, 190, 320.1, 287.1
See application file for complete search history.

(56) References Cited

U.S. PATENT DOCUMENTS

| | | |
|---|---|---|
| 2006/0063217 A1 | 3/2006 | Omura et al. |
| 2008/0003628 A1 | 1/2008 | Kitabayashi et al. |
| 2008/0220460 A1 | 9/2008 | Kawaminami et al. |
| 2011/0318810 A1 | 12/2011 | Tajima et al. |
| 2012/0122130 A1 | 5/2012 | Omura et al. |
| 2012/0244565 A1 | 9/2012 | Nishio et al. |

FOREIGN PATENT DOCUMENTS

| | | |
|---|---|---|
| JP | 2007-289148 A | 11/2007 |
| JP | 2008-237210 A | 10/2008 |
| WO | 2004/058958 A1 | 7/2004 |
| WO | 2006/101239 A1 | 9/2006 |
| WO | 2008/059777 A1 | 5/2008 |
| WO | 2010/053161 A1 | 5/2010 |
| WO | 2010/140431 A1 | 12/2010 |
| WO | 2011/004654 A1 | 1/2011 |
| WO | 2011/068050 A1 | 6/2011 |

OTHER PUBLICATIONS

Devos et al. Practical Limits of Function Prediction Proteins: Structure, Function, and Genetics 41:98-107 (2000).*
Whisstock et al Prediction of protein function from protein sequence and structure Q Rev Biophys. Aug. 2003;36(3):307-40.*
Witkowski et al. Conversion of a â-Ketoacyl Synthase to a Malonyl Decarboxylase by Replacement of the Active-Site Cysteine with Glutamine (Biochemistry 38:11643-11650, 1999.*
Seffernick et al., Melamine Deaminase and Atrazine Chlorohydrolase: 98 Percent Identical but Functionally Different J. Bacteriol. 183(8):2405-2410, 2001.*
Chica et al Semi-rational approaches to engineering enzyme activity: combining the benefits of directed evolution and rational design Curr. Opin. Biotechnol., 2005, vol. 16: 378-384.*
Sen et al.,Developments in Directed Evolution for Improving Enzyme Functions Appl. Biochem. Biotechnol., 2007, vol. 143: 212-223.*
Bak, Tchan-Gi, et al., *Biochim. Biophys. Acta*, 139(2): 265-276 (1967).
Bak, Tchan-Gi, *Biochim. Biophys. Acta*, 139(2): 277-293 (1967).
Bak, Tchan-Gi, *Biochim. Biophys. Acta*, 146(2): 317-327 (1967).
Bak, Tchan-Gi, et al., *Biochim. Biophys. Acta*, 146(2): 328-335 (1967).
Hayano et al., *The Journal of Biological Chemistry*, 242(16): 3665-3672 (1967).
Tsugawa et al., *Applied Biochemistry and Biotechnology*, 56: 301-310 (1996).
Tsugawa et al., *Enzyme and Microbial Technology*, 22(4): 269-274 (1998).
Japanese Patent Office, International Search Report in International Patent Application No. PCT/JP2012/070385 (Sep. 4, 2012), English translation.

* cited by examiner

*Primary Examiner* — Kagnew H Gebreyesus
(74) *Attorney, Agent, or Firm* — Leydig, Voit & Mayer, Ltd.

(57) ABSTRACT

An object of the present invention is to provide a novel glucose dehydrogenase, a method for producing the glucose dehydrogenase, and applications of the glucose dehydrogenase. An isolated flavin-binding glucose dehydrogenase comprising a polypeptide having an amino acid sequence with 80% or more identity to the amino acid sequence of SEQ ID NO: 1, and having glucose dehydrogenase activity is provided.

5 Claims, 6 Drawing Sheets

GLUCOSE DEHYDROGENASE

CROSS-REFERENCE TO RELATED APPLICATIONS

This patent application is a continuation-in-part of International Patent Application No. PCT/JP2012/070385, filed on Aug. 9, 2012, which claims priority to Japanese Patent Application No. 2011-175705, filed on Aug. 11, 2011, Japanese Patent Application No. 2011-222269, filed on Oct. 6, 2011, and Japanese Patent Application No. 2011-222274, filed on Oct. 6, 2011, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 23,927 bytes ASCII (Text) file named "715831Sequence-Listing.txt," created Feb. 7, 2014.

TECHNICAL FIELD

The present invention relates to a glucose dehydrogenase. Specifically, the invention relates to a flavin-binding glucose dehydrogenase, DNA encoding the flavin-binding glucose dehydrogenase, a fungus that produces the flavin-binding glucose dehydrogenase, a method for producing the flavin-binding glucose dehydrogenase, a method for measuring glucose using the flavin-binding glucose dehydrogenase, and the like.

BACKGROUND ART

Self-monitoring of blood glucose (SMBG) is important for diabetic patients to manage their blood glucose levels and to use this monitoring in treatment. Simple blood glucose self-monitoring devices using an electrochemical biosensor have recently been widely used in SMBG. The biosensor includes an insulating substrate on which electrodes and an enzyme reaction layer are formed.

Examples of enzymes used herein include glucose dehydrogenase (GDH), glucose oxidase (GO), and the like. In terms of methods using GO (EC 1.1.3.4), a problem has been noted in that dissolved oxygen in a measurement sample is likely to affect the measurement results. Methods using GDH are also not suitable for accurately measuring blood glucose levels, because although a pyrroloquinoline quinone-dependent glucose dehydrogenase (PQQ-GDH) (EC1.1.5.2 (formerly EC1.1.99.17)) is unaffected by dissolved oxygen, PQQ-GDH acts on sugars, such as maltose and lactose, in addition to glucose.

A flavin adenine dinucleotide-dependent glucose dehydrogenase (hereinafter also referred to as "FADGDH") is unaffected by dissolved oxygen and has almost no action on maltose. According to Patent Documents 1 to 6 and Non-patent Documents 1 to 6, enzymes derived from *Aspergillus terreus* and *Aspergillus oryzae*, and modifications of these, are known. These enzymes, however, have relatively high reactivity to xylose (Patent Document 1), and there is therefore room for improvement in measuring blood glucose of people who are undergoing a xylose tolerance test.

To solve these problems, a modified GDH having a combination of advantages of GO and GDH (Patent Document 7), and the like, have currently been developed.

CITATION LIST

Patent Documents

Patent Document 1: WO2004/058958
Patent Document 2: WO2006/101239
Patent Document 3: JP2007-289148A
Patent Document 4: JP2008-237210A
Patent Document 5: WO2008/059777
Patent Document 6: WO2010/140431
Patent Document 7: WO2011/068050

Non-Patent Documents

Non-patent Document 1: Biochim Biophys Acta. 1967 Jul. 11; 139 (2): 265-76
Non-patent Document 2: Biochim Biophys Acta. 1967 Jul. 11; 139 (2): 277-93
Non-patent Document 3: Biochim Biophys Acta. 146 (2): 317-27
Non-patent Document 4: Biochim Biophys Acta. 146 (2): 328-35
Non-patent Document 5: J Biol Chem (1967) 242: 3665-3672
Non-patent Document 6: Appl Biochem Biotechnol (1996) 56: 301-310

SUMMARY OF INVENTION

Technical Problem

Under the above circumstances, the present inventors conducted intensive research to develop a novel glucose dehydrogenase that is more suitable for use in SMBG, and found that the use of an enzyme that has excellent substrate specificity and high affinity for D-glucose enables shortening the measurement time while accurately measuring blood glucose levels with a small amount of enzyme.

Solution to Problem

The present inventors conducted intensive research to achieve the above use. As a result of screening many microorganisms that had not been reported to produce glucose dehydrogenase, they found that microorganisms that belong to the genus *Circinella* have glucose dehydrogenase activity. The present inventors then conducted further research. Specifically, they isolated and purified a flavin-binding GDH produced by the microorganisms that belong to the genus *Circinella*, analyzed its properties, and thereby found that the flavin-binding GDH has excellent substrate specificity and high affinity for D-glucose. Further, the present inventors determined the amino acid sequence and gene sequence of the isolated enzyme, and ascertained that these sequences are different from those of already reported FADGDH, and that the isolated enzyme is novel.

The present inventions have been accomplished as a result of further research and improvement based on these findings. Representative examples of the invention are described below.

Item 1. A flavin-binding glucose dehydrogenase having the following properties (1) and (2):

(1) Molecular weight: the molecular weight of a polypeptide moiety in the enzyme is about 70 kDa as measured by SDS-polyacrylamide electrophoresis; and (2) Km value: the Km value for D-glucose is about 20 mM or less.

Item 2. The flavin-binding glucose dehydrogenase according to Item 1, further having the following property (3):

(3) Substrate specificity: the reactivity to D-xylose is 1.7% or less, based on the reactivity to D-glucose taken as 100%.

Item 3. The flavin-binding glucose dehydrogenase according Item 1 or 2, further having the following property (4):

(4) Optimal activity temperature: 37 to 45° C.

Item 4. The flavin-binding glucose dehydrogenase according to any one of Items 1 to 3, further having one or more properties selected from the group consisting of the following properties (5) to (7):

(5) Optimal activity pH: 6.5;
(6) pH stability: stable at a pH range of 5 to 7; and
(7) Temperature stability: stable at a temperature of 40° C. or less.

Item 5. The flavin-binding glucose dehydrogenase according to any one of Items 1 to 4, further having the following property (8):

(8) Origin: the enzyme is derived from microorganisms of the genus *Circinella*.

Item 6. A method for producing the flavin-binding glucose dehydrogenase of any one of Items 1 to 5, the method comprising:

culturing microorganisms of the genus *Circinella*; and
recovering a glucose dehydrogenase.

Item 7. A flavin-binding glucose dehydrogenase comprising any one of the following polypeptides (a) to (c):

(a) a polypeptide having an amino acid sequence of SEQ ID NO: 1, (b) a polypeptide having the amino acid sequence of SEQ ID NO: 1 in which one or several amino acid residues are substituted, deleted, inserted, added, and/or inverted, and having glucose dehydrogenase activity; and (c) a polypeptide having an amino acid sequence with 80% or more identity to the amino acid sequence of SEQ ID NO: 1, and having glucose dehydrogenase activity.

Item 8. A DNA of any one of the following (A) to (F):

(A) DNA encoding an amino acid sequence of SEQ ID NO: 1;

(B) DNA having a base sequence of SEQ ID NO: 2;

(C) DNA having a base sequence with 80% or more homology to the base sequence of SEQ ID NO: 2, and encoding a polypeptide having glucose dehydrogenase activity;

(D) DNA hybridizing to a base sequence complementary to the base sequence of SEQ ID NO: 2 under stringent conditions, and encoding a polypeptide having glucose dehydrogenase activity;

(E) DNA having the base sequence of SEQ ID NO: 2 in which one or several bases are substituted, deleted, inserted, added, and/or inverted, and encoding a polypeptide having glucose dehydrogenase activity; and (F) DNA having the amino acid sequence of SEQ ID NO: 1 in which one or several amino acid residues are substituted, deleted, inserted, added, or inverted, and encoding a polypeptide having glucose dehydrogenase activity.

Item 9. A vector containing the DNA of Item 8.
Item 10. A transformant containing the vector of Item 9.
Item 11. A method for producing the flavin-binding glucose dehydrogenase of Item 7, the method comprising culturing the transformant of Item 10.

Item 12. A method for measuring a glucose concentration, the method comprising causing the flavin-binding glucose dehydrogenase of any one of Items 1 to 5 and 7 to act on glucose.

Item 13. A glucose assay kit comprising the flavin-binding glucose dehydrogenase of any one of Items 1 to 5 and 7.

Item 14. A glucose sensor comprising the flavin-binding glucose dehydrogenase of any one of Items 1 to 5 and 7.

Item 15. A flavin-binding glucose dehydrogenase comprising a polypeptide having an amino acid sequence with 80% or more identity to the amino acid sequence of SEQ ID NO: 1, and having glucose dehydrogenase activity, wherein the polypeptide does not comprise the amino acid sequence of SEQ ID NO: 1.

Item 16. A flavin-binding glucose dehydrogenase comprising a polypeptide having an amino acid sequence with 80% or more identity to the amino acid sequence of SEQ ID NO: 1, and having glucose dehydrogenase activity, wherein the polypeptide is obtained by recombinantly expressing a DNA encoding a polypeptide having 80% or more identity with the amino acid sequence of SEQ ID NO: 1.

Item 17. The flavin-binding glucose dehydrogenase of Item 16, wherein the recombinant expression of the DNA comprises:

preparing a recombinant vector comprising a DNA encoding a polypeptide having 80% or more identity with the amino acid sequence of SEQ ID NO: 1, introducing the recombinant vector into a cell, and
cultivating the cell.

Item 18. The flavin-binding glucose dehydrogenase of Item 17, wherein the cell is not *Circinella simplex* NBRC6412.

Item 19. A DNA having a base sequence with 80% or more homology to the base sequence of SEQ ID NO: 2, and encoding a polypeptide having glucose dehydrogenase activity, wherein the DNA does not comprise the base sequence of SEQ ID NO: 2.

Item 20. The DNA of Item 19, wherein the codon frequency of the DNA is optimized for expression in a cell other than genus *Circinella*.

Advantageous Effects of Invention

The flavin-binding glucose dehydrogenase (hereinafter sometimes referred to as "FGDH") of the invention has glucose dehydrogenase activity and high affinity for D-glucose (i.e., has a significantly small Km value for D-glucose), and thus enables measurement of D-glucose concentration in a sample in a shorter period of time with a smaller amount of enzyme. Additionally, since the FGDH of the invention has significantly reduced reactivity to D-xylose, even when D-glucose and D-xylose are both present in a sample, the amount and the concentration of glucose can be accurately measured. As such, the FGDH of the invention can accurately measure glucose concentration in any sample containing D-glucose (e.g., blood and food (such as seasonings and beverages)). Further, the DNA of the invention encodes the FGDH of the invention, and the FGDH of the invention can thus be efficiently produced by using genetic engineering techniques.

BRIEF DESCRIPTION OF DRAWINGS

In FIG. 1, lane 1 shows molecular weight markers, and lane 2 shows purified enzyme.

In FIG. 2, lane 1 shows molecular weight markers, and lane 2 shows purified enzyme treated with N-glycosidase F.

FIG. 3-1 is a graph showing the influence of pH on the activity of NBRC6412-derived FGDH.

FIG. 3-2 is a graph showing the influence of pH on the activity of RD055422-derived FGDH.

FIG. 4-1 is a graph showing the influence of temperature on the activity of NBRC6412-derived FGDH.

FIG. 4-2 is a graph showing the influence of temperature on the activity of RD055422-derived FGDH.

FIG. 5-1 is a graph showing the measurement results of the pH stability of NBRC6412-derived FGDH.

FIG. 5-2 is a graph showing the measurement results of the pH stability of RD055422-derived FGDH.

FIG. 6-1 is a graph showing the measurement results of the thermal stability of the NBRC6412-derived FGDH.

FIG. 6-2 is a graph showing the measurement results of the thermal stability of RD055422-derived FGDH.

FIG. 7-1 shows a Lineweaver-Burk plot regarding D-glucose of NBRC6412-derived FGDH.

FIG. 7-2 shows a Lineweaver-Burk plot regarding D-glucose of RD055422-derived FGDH.

DESCRIPTION OF EMBODIMENTS

Figure 1:
FIG. 1 shows the results of SDS-PAGE of FGDH purified from *Circinella simplex* NBRC6412 strain.

The present invention is described below in detail.
1. Flavin-Binding Glucose Dehydrogenase
1-1. Glucose Dehydrogenase Activity A flavin-binding glucose dehydrogenase is an enzyme that has a physicochemical property such that it catalyzes a reaction in which hydroxy groups of glucose are oxidized to produce glucono-δ-lactone in the presence of an electron acceptor. In this specification, this physicochemical property represents glucose dehydrogenase activity, and the terms "enzyme activity" and "activity" represent this enzyme activity, unless otherwise noted. The electron acceptor is not limited as long as it can accept electrons in a reaction catalyzed by FGDH. For example, 2,6-dichlorophenolindophenol (DCPIP), phenazine methosulfate (PMS), 1-methoxy-5-methylphenazium methylsulfate, and ferricyanide compounds may be used.

The glucose dehydrogenase activity can be measured by known methods. For example, the activity can be measured using DCPIP as an electron acceptor and based on the change in absorbance of a sample at a wavelength of 600 nm before and after the reaction. More specifically, the activity can be measured using the following reagent and under the following measurement conditions.

Method for Measuring Glucose Dehydrogenase Activity
Reagent
  50 mM PIPES buffer solution, pH of 6.5 (containing 0.1% TritonX-100)
  24 mM PMS solution
  2.0 mM 2,6-dichlorophenolindophenol (DCPIP) solution
  1 M D-glucose solution The reaction reagent is obtained by mixing 20.5 mL of the PIPES buffer solution, 1.0 mL of the DCPIP solution, 2.0 mL of the PMS solution, and 5.9 mL of the D-glucose solution.

Measurement Conditions

The reaction reagent (3 mL) is preheated at 37° C. for 5 minutes. An FGDH solution (0.1 mL) is added and gently mixed. Water is used as a control, and changes in absorbance at 600 nm are recorded for 5 minutes by a spectrophotometer at a controlled temperature of 37° C. Based on the linear portion (i.e., after the reaction rate becomes constant), the change in absorbance per minute ($\Delta OD_{TEST}$) is measured. In a blind test, a solvent used for dissolving FGDH is added to the reagent mixture in place of the FGDH solution, and the change in absorbance per minute ($\Delta OD_{BLANK}$) is measured in a similar manner. Based on the obtained values, the FGDH activity is determined by the following equation. Here, one unit (U) of the FGDH activity is equal to the enzyme amount that reduces 1 μmol of DCPIP in 1 minute in the presence of D-glucose at a concentration of 200 mM.

$$\text{Activity (U/mL)} = \{-(\Delta OD_{TEST} - \Delta OD_{BLANK}) \times 3.1 \times \text{dilution rate}\}/\{16.3 \times 0.1 \times 1.0\}$$

In the equation, 3.1 is the total liquid amount (mL) of the reaction reagent and the enzyme solution, 16.3 is the millimolar extinction coefficient ($cm^2$/pmol) under conditions in which the activity is measured, 0.1 is the amount (mL) of the enzyme solution, and 1.0 is the optical path length (cm) of the cell. In this specification, the enzyme activity is measured according to the above measurement method, unless otherwise indicated.

The FGDH of the invention refers to flavin-binding GDH, which requires flavin as a prosthetic group.

The FGDH of the invention is preferably isolated FGDH or purified FGDH. The FGDH of the invention may be in a state of being dissolved in a solution described above that is suitable for storage or in a freeze-dried state (e.g., powder). The expression "isolated" used in regard to the enzyme (FGDH) of the invention refers to a state in which the enzyme is substantially free of components (e.g., host-cell-derived contaminating proteins, other components, and culture media) other than the enzyme. Specifically, for example, the isolated enzyme of the invention contains contaminating proteins in an amount of less than about 20%, preferably less than about 10%, more preferably less than about 5%, even more preferably less than about 1%, of the total (by weight). It is also possible for the FGDH of the invention to be present in a solution (e.g., buffer) suitable for storage or for measurement of enzyme activity.

1-2. Polypeptide

The FGDH of the invention preferably comprises any one of the following polypeptides (a) to (c):

(a) a polypeptide having the amino acid sequence of SEQ ID NO: 1;
(b) a polypeptide having the amino acid sequence of SEQ ID NO: 1 in which one or several amino acid residues are substituted, deleted, inserted, added, and/or inverted, and having glucose dehydrogenase activity; and
(c) a polypeptide having an amino acid sequence with 80% or more identity to the amino acid sequence of SEQ ID NO: 1, and having glucose dehydrogenase activity.

As shown in Example 5, the amino acid sequence of SEQ ID NO: 1 is equal to the amino acid sequence of FGDH derived from *Circinella simplex* NBRC6412. The FGDH derived from *Circinella* simplex NBRC6412 exhibits all the properties described in Sections 1-3 to 1-8 below.

The polypeptide described in (b) above has the amino acid sequence of SEQ ID NO: 1 in which one or several amino acid residues are substituted, deleted, inserted, added, and/or inverted (hereinafter sometimes collectively referred to as "mutation"), as long as the glucose dehydrogenase activity is not impaired. The term "several" as used herein indicates a number corresponding to, for example, less than about 20%, preferably less than about 15%, still more preferably less than about 10%, even more preferably less than about 5%, and the most preferably less than about 1%, of the total amino acids, although such a number is not limited as long as the glucose dehydrogenase activity and preferably the properties described in Sections 1-3 to 1-10 (in particular, Sections 1-3 and 1-4) below are not impaired. More specifically, for example, the number is 2 to 127, preferably 2 to 96, more preferably 2 to 64, still more preferably 2 to 32, even more preferably 2 to 20, further preferably 2 to 15, yet further preferably 2 to 10, and the most preferably 2 to 5.

Specific examples of the polypeptide described in (b) above include a polypeptide having the amino acid sequence of SEQ ID NO: 16. The amino acid sequence of SEQ ID NO: 16 is equal to the amino acid sequence of FGDH derived from *Circinella* RD055422, and differs from the amino acid sequence of SEQ ID NO: 1 only in that the amino acid at position 582 is aspartic acid rather than glycine.

The type of amino acid substitution is not particularly limited, but is preferably a conservative amino acid substitution, because it does not cause a significant effect on the phenotype of FGDH. The "conservative amino acid substitution" refers to a replacement of an amino acid residue with another amino acid residue having a side chain with similar properties. Amino acid residues are grouped into various families according to their side chains, such as basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). The conservative amino acid substitution is preferably a replacement between amino acid residues of the same family.

One or more mutations can be performed by introducing one or more mutations into DNA encoding the FGDH of the invention (mentioned below) by using known techniques, such as restriction enzyme treatment, treatment with exonuclease, DNA ligase, or the like, a site-directed mutagenesis induction method (Molecular Cloning, Third Edition, Chapter 13, Cold Spring Harbor Laboratory Press, New York), a random mutagenesis introduction method (Molecular Cloning, Third Edition, Chapter 13, Cold Spring Harbor Laboratory Press, New York), and the like. Other methods, such as ultraviolet irradiation, may also be used to produce variant FGDH. Variant FGDH also includes naturally occurring variants (e.g., single nucleotide polymorphism), for example, based on individual variability of microorganisms carrying FGDH, or on difference in species or families of those microorganisms.

In terms of maintaining the FGDH activity, the one or more mutations above preferably present in sites that do not influence the FGDH active site or substrate binding site.

The polypeptide described in (c) above is a polypeptide having an amino acid sequence with 80% or more identity to the amino acid sequence of SEQ ID NO: 1, as long as the glucose dehydrogenase activity and preferably the properties described in Sections 1-2 to 1-8 above are maintained. The amino acid sequence of the FGDH of the invention preferably has 85% or more, more preferably 88% or more, still more preferably 90% or more, even more preferably 93% or more, further preferably 95% or more, particularly preferably 98% or more, and the most preferably 99% or more, identity to the amino acid sequence of SEQ ID NO: 1. A polypeptide having an amino acid sequence with a specific degree of identity can be produced based on known genetic engineering techniques mentioned above. Specific examples of the polypeptide described in (c) include a polypeptide having the amino acid sequence of SEQ ID NO: 16.

In a preferred embodiment, the FADGDH having at least 80% or more identity to the amino acid sequence of SEQ ID NO: 1 preferably does not comprise the amino acid sequence that is identical to the sequence of SEQ ID NO: 1 because such an altered FADGDH may possess an improved characteristic compared to the FADGDH having the sequence of SEQ ID NO: 1.

In another embodiment, it is preferred that an FADGHD having at least 80% identity to the sequence of SEQ ID NO:2 is obtained by recombinantly expressing a DNA encoding polypeptide having at least 80% identity to the sequence of SEQ ID NO: 2 in a cell other than *Circinella simplex* NBRC6412. The FADGDH obtained through such a recombinant expression of a gene encoding thereof is structurally different from the FADGDH obtained from *Circinella simplex* NBRC6412, for example, with respect to sugar chains bound to the FADGDH. The difference mainly results from the host cell used for the recombinant expression because the sugar chain pattern is unique to the host cell.

The amino acid sequence identity can be calculated using a commercially available analytical tool or an analytical tool available through telecommunication lines (Internet). For example, the online homology algorithm Basic Local Alignment Search Tool (BLAST program) of the National Center for Biotechnology Information (NCBI), available at www.ncbi.nlm.nih.gov/BLAST/, may be used for the calculation using parameters with default (initial) settings.

1-3. Substrate Specificity

The FGDH of the invention has excellent substrate specificity. In particular, the FGDH of the invention has significantly reduced reactivity at least to D-xylose, compared to the reactivity to D-glucose. More specifically, the FGDH of the invention has reactivity to D-xylose of preferably 1.7% or less, more preferably 1.6% or less, still more preferably 1.3% or less, and even more preferably 1.2% or less, based on the reactivity to D-glucose at the same concentration taken as 100%.

In addition to the low reactivity to D-xylose, it is preferable that the FGDH of the invention also has low reactivity to D-galactose and maltose. The FGDH of the invention has reactivity to D-galactose of generally 5% or less, preferably 3% or less, more preferably 2% or less, still more preferably 1.1% or less, and particularly preferably 0.5% or less, based on the reactivity to D-glucose at the same concentration taken as 100%.

The FGDH of the invention has reactivity to maltose of generally 5% or less, preferably 3% or less, more preferably 2% or less, still more preferably 1% or less, and particularly preferably 0.6% or less, based on the reactivity to D-glucose at the same concentration taken as 100%.

The lower limit of the reactivity of the FGDH of the invention to D-xylose, D-galactose, or maltose, based on the reactivity to D-glucose, is not particularly limited, but may be set to 0% or a value closest to 0%.

The reactivity of FGDH to each sugar can be measured by replacing D-glucose with another sugar (e.g., D-xylose, D-galactose, or maltose) in the method for measuring the glucose dehydrogenase activity described in Section 1-1 above, and comparing the results with the results of the D-glucose activity. For comparison, the concentration of each sugar is 50 mM.

The FGDH of the invention having such excellent substrate specificity is preferably used as an enzyme for accurately measuring the amount of glucose in a sample. Specifically, the FGDH of the invention can accurately measure the amount of target D-glucose even when the sample contains impurities, such as maltose, D-galactose, and D-xylose. Therefore, this enzyme of the invention is considered to be suitable for applications where impurities in a sample are a concern or expected (typically, measuring the amount of glucose in blood). In addition to these applications, this enzyme is also applicable to various applications and is highly versatile.

1-4. Affinity for D-Glucose

The FGDH of the invention preferably has high affinity for D-glucose, which is its natural substrate. Due to high affinity, even when a sample contains D-glucose at a low concentration, the catalytic reaction described above can proceed. Further, such high affinity contributes to more accurate measurement of the D-glucose concentration, the measurement in a shorter period of time, and the measurement with the use of smaller amount of enzyme. The affinity of FGDH for D-glucose is expressed as a Km value. A Km value is calculated from a so-called Michaelis-Menten equation. Specifically, a Km value is calculated by varying the D-glucose concentration in the activity measurement method described in Section 1-1 above, and measuring the activity in each concentration to create a Lineweaver-Burk plot.

According to enzyme kinetics, an enzyme having a lower Km value has a higher affinity for a substrate, and the enzyme can form a complex with the substrate even at a low substrate concentration, allowing the catalytic reaction to proceed at a faster rate. The FGDH of the invention has a Km value for D-glucose of preferably 20 mM or less, more preferably 15 mM or less, still more preferably 14 mM or less, even more preferably 13 mM or less, further preferably 12.5 mM or less, still further preferably 10 mM or less, and yet further preferably 8.5 mM or less.

1-5. Optimal Activity PH

In other embodiments, the FGDH of the invention has an optimal activity pH of preferably 6.5, as shown in the Examples below. The optimal activity pH of 6.5 as used herein typically means that the pH is around a value of 6.5 with an acceptable allowance to some extent. As used herein, the optimal activity pH can be determined by measuring the enzyme activity using PIPES-NaOH buffer (enzyme concentration: 100 U/mL), as shown in the Examples below.

1-6. Optimal Activity Temperature

In other embodiments, the FGDH of the invention has an optimal activity temperature of preferably 37 to 45° C. The optimal activity temperature of 37 to 45° C. as used herein typically means that the temperature is more or less within a range of 37 to 45° C., and the range further includes an acceptable allowance to some extent. From another viewpoint, the FGDH of the invention has enzyme activity at 50° C. of preferably 60% or more, and more preferably 65% or more, based on the enzyme activity at 45° C. (100%). From still another viewpoint, the FGDH of the invention has enzyme activity at a temperature range of 30 to 50° C. of preferably 60% or more, and more preferably 65% or more, based on the enzyme activity at 45° C. In this specification, the optimal activity temperature can be calculated by measuring the enzyme activity in PIPES-NaOH buffer (pH 6.5) at an enzyme concentration of 0.1 U/mL, as shown in the Examples below.

1-7. pH Stability

In this specification, when 10 U/mL of enzyme that has been treated at 25° C. for 16 hours under specific pH conditions has remaining enzyme activity of 80% or more, compared to the enzyme activity of the same enzyme before treatment, this enzyme is considered to be stable under these pH conditions. The FGDH of the invention is preferably stable at a pH range of 5 to 7. The FGDH of the invention may be stable at a wider pH range (e.g., pH of 3 to 7), as long as it is stable at a pH range of 5 to 7. In one embodiment, it is more preferable that the FGDH of the invention has remaining enzyme activity of 90% or more when treated as above at a pH range of 5 to 7 or a wider pH range (e.g., pH of 3.5 to 7.5).

1-8. Temperature Stability

In this specification, when 100 U/mL of enzyme that has been treated for 15 minutes in an appropriate buffer solution (e.g., potassium acetate buffer (pH of 5.0)) under specific temperature conditions has remaining enzyme activity that is not substantially reduced, compared to the enzyme activity of the same enzyme before treatment (i.e., when about 90% or more of the enzyme activity remains), this enzyme is considered to be stable under these temperature conditions. The FGDH of the invention is preferably stable at a temperature range of 0 to 40%.

The FGDH of the invention preferably has at least one, more preferably 2 or more, still more preferably 3 or more, even more preferably 4 or more, further preferably 5 or more, yet further preferably 6 or more, and particularly preferably all, of the properties described in Sections 1-3 to 1-8 above and in Section 1-9 below. The FGDH of the invention may have any combination of the properties described in Sections 1-3 to 1-8 above and Section 1-9 below.

1-9. Molecular Weight

In other embodiments, the polypeptide moiety constituting the FGDH of the invention preferably has a molecular weight of about 70 kDa as measured by SDS-PAGE. The "about 70 kDa" includes a range in which a person skilled in the art would usually determine that the band is present at a position of 70 kDa when a molecular weight is measured by SDS-PAGE. The "polypeptide moiety" refers to FGDH substantially not having an attached sugar chain. When the FGDH of the invention produced by microorganisms is in a glycosylated form, heat treatment or glycohydrolase treatment may be performed so that the sugar chains are removed (i.e., so that the "polypeptide moiety" is obtained). The state of "substantially not having an attached sugar chain" allows the existence of sugar chains necessarily remaining after heat treatment or glycohydrolase treatment of the FGDH in a glycosylated form. Therefore, when FGDH is originally not in a glycosylated form, the FGDH itself corresponds to the "polypeptide moiety."

The means for removing sugar chains from FGDH in a glycosylated form is not particularly limited. For example, as shown in the Examples below, the sugar chains can be removed by denaturing the FGDH in a glycosylated form by heat treatment at 100° C. for 10 minutes, followed by treatment at 37° C. for 6 hours with N-glycosidase F (produced by Roche Diagnostics K.K.).

When the FGDH of the invention has an attached sugar chain, its molecular weight is not limited, as long as no adverse effect is made on the glucose dehydrogenase activity, substrate specificity, affinity for D-glucose, or the like. For example, when the FGDH of the invention has an attached sugar chain, the molecular weight is preferably 90,000 to 110,000 Da as measured by SDS-PAGE. The FGDH in a glycosylated form is preferable, considering that it better stabilizes the enzyme, and enhances water solubility to be easily dissolved in water.

The molecular weight measurement by SDS-PAGE may be performed using general techniques and devices with the use of commercially available molecular weight markers.

1-10. Origin

The typical FGDH of the invention is isolated from microorganisms that belong to the genus *Circinella*. The FGDH of the invention thus preferably originates from microorganisms that belong to the genus *Circinella*. Specific examples of microbial species classified into the genus *Circinella* from which the FGDH of the invention can be derived include *Circinella minor*, *Circinella mucoroides*, *Circinella muscae*, *Circinella rigida*, *Circinella simplex*, *Circinella umbellata*, and the like. Specific strains to which these species belong include *Circinella minor* NBRC6448, *Circinella mucoroides* NBRC4453, *Circinella muscae* NBRC6410, *Circinella rigida* NBRC6411, *Circinella simplex* NBRC6412, *Circinella umbellata* NBRC4452, *Circinella umbellata* NBRC5842, *Circinella* RD055423, *Circinella* RD055422, and the like. Of these, the FGDH of the invention preferably originates from *Circinella simplex* NBRC6412 or *Circinella* RD055422.

2. DNA Encoding Flavin-Binding Glucose Dehydrogenase

The DNA of the invention encodes the FGDH described in Section 1 above. Specifically, the DNA of the invention is any one of the following (A) to (F):

(A) DNA encoding the amino acid sequence of SEQ ID NO: 1;
(B) DNA having the base sequence of SEQ ID NO: 2;
(C) DNA having a base sequence with 80% or more homology to the base sequence of SEQ ID NO: 2, and encoding a polypeptide having glucose dehydrogenase activity;
(D) DNA hybridizing to a base sequence complementary to the base sequence of SEQ ID NO: 2 under stringent conditions, and encoding a polypeptide having glucose dehydrogenase activity;
(E) DNA having the base sequence of SEQ ID NO: 2 in which one or several bases are substituted, deleted, inserted, added, and/or inverted, and encoding a polypeptide having glucose dehydrogenase activity; and
(F) DNA having the amino acid sequence of SEQ ID NO: 1 in which one or several amino acid residues are substituted, deleted, inserted, added, or inverted, and encoding a polypeptide having glucose dehydrogenase activity.

As used herein, the phrase "DNA encoding a protein" refers to DNA from which the protein is obtained when the DNA is expressed. Specifically, the "DNA encoding a protein" refers to DNA having a base sequence corresponding to the amino acid sequence of the protein. Therefore, the "DNA encoding a protein" also includes the DNA that varies according to codon degeneracy.

The DNA of the invention has a base sequence with 80% or more, preferably 85% or more, more preferably 88% or more, still more preferably 90% or more, even more preferably 93% or more, further preferably 95% or more, particularly preferably 98% or more, and most preferably 99% or more, homology to the base sequence of SEQ ID NO: 2, as long as the protein having the amino acid sequence encoded by this DNA has glucose dehydrogenase activity and preferably at least one property from among the properties described in Sections 1-3 to 1-8 above (particularly properties described in Sections 1-3 and 1-4). Specific examples of such DNA of the invention include DNA having the base sequence of SEQ ID NO: 17. The base sequence of SEQ ID NO: 17 codes for FGDH derived from *Circinella* RD055422, and differs only in 5 bases from the base sequence of SEQ ID NO: 2.

In a preferred embodiment, the DNA having a base sequence with 80% or more homology to the base sequence of SEQ ID NO: 2 and encoding a polypeptide with a FADGDH activity does not comprise the base sequence identical to the sequence of SEQ ID NO: 2. Such an altered DNA may encode a FADGDH with an improved characteristic compared to the FADGDH having the amino acid sequence of SEQ ID NO: 1. The altered DNA may also be preferred because the codon frequency of the DNA may be optimized with respect to the type of a cell within which the DNA is expressed.

The base sequence homology can be calculated using a commercially available analytical tool or an analytical tool available through telecommunication lines (Internet). For example, software, such as FASTA, BLAST, PSI-BLAST, or SSEARCH, is used for the calculation. Specifically, the main initial conditions generally used in a BLAST search are as follows: in Advanced BLAST 2.1, a blastn program is used, and the parameters are set to default values to perform a search to thereby obtain a homology value (%) of a nucleotide sequence.

The DNA of the invention may be DNA hybridizing to a base sequence complementary to the base sequence of SEQ ID NO: 2 under stringent conditions, as long as the protein coded by this DNA has glucose dehydrogenation activity and preferably at least one property from among properties described in Sections 1-2 to 1-8 above. The "stringent conditions" as used herein refer to conditions under which a specific hybrid is formed, while a non-specific hybrid is not formed. Such stringent conditions are known to a person skilled in the art and may be established with reference to, for example, Molecular Cloning (Third Edition, Cold Spring Harbor Laboratory Press, New York) or Current Protocols in Molecular Biology (edited by Frederick M. Ausubel et al., 1987).

Examples of specific stringent conditions include conditions in which a hybridization solution (50% formamide, 10×SSC (0.15 M NaCl, 15 mM sodium citrate, pH of 7.0), 5×Denhardt's solution, 1% SDS, 10% dextran sulfurate, 10 µg/mL of denatured salmon sperm DNA, and 50 mM phosphoric acid buffer (pH of 7.5)) is used, and incubation is carried out at about 42 to 50° C., followed by washing at about 65 to 70° C. with 0.1×SSC and 0.1% SDS. More preferable examples of the stringent conditions include conditions in which 50% formamide, 5×SSC (0.15 M NaCl, 15 mM sodium citrate, pH of 7.0), 1×Denhardt's solution, 1% SDS, 10% dextran sulfate, 10 µg/mL of denatured salmon sperm DNA, and 50 mM phosphoric acid buffer (pH of 7.5) are used as a hybridization solution.

DNA that undergoes hybridization under the above conditions possibly includes DNA containing a stop codon in the middle, or DNA whose activity is abolished as a result of the mutation in the active center. However, such DNA can be easily removed by introducing it into a commercially available active expression vector, expressing it in a suitable host, and determining the enzyme activity using known techniques.

In terms of the DNA described in (E) and (F) above, the term "several" is as defined in Section 1-2 above.

In a preferable embodiment, DNA encoding the FGDH of the invention is present in an isolated state. As used herein, DNA in an "isolated" state means that the DNA is separated from components such as other nucleic acids and proteins that coexist in nature. However, it is possible for the DNA to contain a portion of other nucleic acid components, such as nucleic acid sequences (e.g., promoter region sequences and terminator sequences) that naturally flank the DNA sequence. For example, chromosomal DNA in an isolated state is preferably substantially free of other DNA components coexisting in nature. When DNA prepared by genetic engineering techniques, such as cDNA molecules, is in an isolated state, it is preferably substantially free of cell components, culture media, and the like. Likewise, when DNA prepared by chemical synthesis is in an isolated state, it is preferably substantially free of precursors (starting materials) such as dNTP, as well as chemical substances, etc., used in the synthetic process. When referred to simply as "DNA" in this specification, it means that the DNA is in an isolated state, unless otherwise clearly stated that it has a different meaning. The DNA of the invention includes DNA (cDNA) complementary to the DNAs described in (A) to (F) above.

The DNA of the invention may be produced or obtained by chemical DNA synthesis based on this specification or the sequence information (in particular SEQ ID NO: 2) in the accompanying Sequence Listing. It is also possible to easily prepare the DNA of the invention by using standard genetic engineering techniques, molecular biological techniques, biochemical techniques, and the like (see Molecular Cloning 2nd Ed, Cold Spring Harbor Lab. Press (1989); *Zoku-Seikagaku Jikken Kouza, Idenshi Kenkyuho* I, II, III, [Sequel Biochemical Experiment Lecture, Gene Study Methods I, II, III], 1986, Japanese Biochemical Society ed.; etc.). Examples of chemical DNA synthesis include solid-phase synthesis using a phosphoramidite method. An automated synthesis device may be used in this synthesis.

Standard genetic engineering techniques can be performed, specifically, by preparing a cDNA library from suitable source microorganisms that can express the FGDH of the invention according to a known method, and selecting desired clones using an appropriate probe or antibody specific to the DNA sequence of the invention (e.g., the base sequence of SEQ ID NO: 2) from this library (Proc. Natl. Acad. Sci., U.S.A., 78, 6613; (1981) Science 122, 778 (1983), etc.).

The source microorganisms for preparing a cDNA library are not limited, as long as they express the FGDH of the invention, but are preferably microorganisms of the genus *Circinella*. Preferable examples of *Circinella* species suitable as source microorganisms include *Circinella minor, Circinella mucoroides, Circinella muscae, Circinella rigida, Circinella simplex, Circinella umbellata*, and the like. More specific examples of source microbial strains include *Circinella minor* NBRC6448, *Circinella mucoroides* NBRC4453, *Circinella muscae* NBRC6410, *Circinella rigida* NBRC6411, *Circinella simplex* NBRC6412, *Circinella umbellata* NBRC4452, *Circinella umbellata* NBRC5842, *Circinella* RD055423, *Circinella* RD055422, and the like. Of these, *Circinella simplex* NBRC6412 and *Circinella* RD055422 are preferable.

Separation of total RNA from the above microorganisms, separation and purification of mRNA, production and cloning of cDNA, and the like, may all be carried out using known methods. Methods for screening cDNA libraries for the DNA of the invention are also not limited and can be performed using usual methods. For example, a method may be used in which an immunological screening is performed by using antibodies specific to a polypeptide derived from cDNA to select the corresponding cDNA clones. It is also possible to use a plaque hybridization method or a colony hybridization method using probes that selectively bind to the target nucleotide sequence. Combinations of these methods may also be used.

In obtaining DNA, it is preferable to use PCR (Science 130, 1350 (1985)) or modified versions of PCR, such as DNA or RNA amplification methods. If obtaining full-length cDNA from libraries is difficult, it is preferable to use a RACE method (Rapid amplification of cDNA ends; Jikken Igaku [Experimental medicine], 12 (6), 35 (1994)), in particular, a 5'-RACE method (M. A. Frohman, et al., Proc. Natl. Acad. Sci., U.S.A., 8, 8998 (1988)), or the like.

The primers used in PCR may also be suitably designed and synthesized based on the base sequence of SEQ ID NO: 2. As described above, amplified DNA or RNA fragments may be isolated and purified according to known methods, such as gel electrophoresis and hybridization.

The use of the DNA of the invention enables easy and stable production of the FGDH of the invention in large amount.

3. Vector

The vector of the invention contains the DNA encoding the FGDH of the invention described in Section 2 above. The "vector" as used herein is not particularly limited in terms of the type and the structure, insofar as it is a nucleic acid molecule (carrier) that can transfer an inserted nucleic acid molecule to a target such as a cell, it can replicate the DNA of the invention in a suitable host cell, and it can express the DNA of the invention. Specifically, the vector of the invention is an expression vector. An appropriate type of vector is selected in consideration of the type of host cell. Specific examples of vectors include plasmid vectors, cosmid vectors, phage vectors, viral vectors (e.g., adenoviral vectors, adeno-associated viral vectors, retroviral vectors, herpesviral vectors), and the like. Vectors suitably used when filamentous fungi are used as hosts may also be used. It is also possible to use vectors suitable for self-cloning.

In the use of *Escherichia coli* as a host, for example, an M13 phage or modifications thereof, a λ phage or modifications thereof, and pBR322 or modifications thereof (e.g., pB325, pAT153, pUC8) may be used. In the use of yeasts as hosts, pYepSec1, pMFa, pYES2, and the like, may be used. In the use of insect cells as hosts, for example, pAc and pVL may be used. In the use of mammalian cells as hosts, for example, pCDM8 and pMT2PC may be used. However, the vectors are not limited to these examples.

An expression vector usually contains, for example, a promoter sequence required for expression of inserted nucleic acid, and an enhancer sequence for facilitating the expression. It is also possible to use an expression vector containing a selection marker. In the use of such an expression vector, whether the expression vector is introduced (and the degree of the introduction) can be confirmed using the selection marker. Insertion of the DNA of the invention into a vector, insertion of a selection marker gene (if required), insertion of a promoter (if required), and the like, may be performed using standard recombinant DNA technology (e.g., well-known methods that use restriction enzymes and DNA ligase, with reference to Molecular Cloning, Third Edition, 1.84, Cold Spring Harbor Laboratory Press, and New York).

4. Transformant

The present invention also relates to a transformant obtained by introducing the DNA of the invention into a host cell. The means for introducing the DNA of the invention into a host cell is not particularly limited. For example, the DNA contained in a vector described in Section 3 above is introduced into a host cell. Host cells are not particularly limited as long as they can express the DNA of the invention to produce FGDH. Specifically, it is possible to use prokaryotic cells, such as *Escherichia coli* and *Bacillus subtilis*; and eukaryotic cells, such as yeast, mold, insect cells, and mammal cells.

Examples of *Escherichia coli* used as a host include *Escherichia coli* C600, *Escherichia coli* HB101, *Escherichia coli* DH5α, and the like, and examples of the vectors include pBR322, pUC19, pBluescript, and the like. Examples of yeast used as a host include *Saccharomyces cerevisiae, Schizosaccharomyces pombe, Candida utilis, Pichia pastoris*, and the like, and examples of the vectors include pAUR101, pAUR224, pYE32, and the like. Examples of filamentous fungal cells used as a host include *Aspergillus oryzae, Aspergillus niger, Circinella simplex*, and the like. Additionally, as a host, it is also preferable to use microorganisms that belong to the genus *Circinella* from which the FGDH is isolated. Specifically, although in transformants, foreign DNA is generally present in a host cell, a preferable embodiment also includes transformants obtained by a self-cloning in which microorganisms from which the DNA is derived is used as a host.

The transformant of the invention is preferably obtained by transfection or transformation of the expression vector described in Section 3 above. The transformation may be transient or stable transformation. Transfection or transformation may be performed by a calcium phosphate co-sedimentation method, an electroporation method (Potter, H. et al., Proc. Natl. Acad. Sci. U.S.A. 81, 7161-7165 (1984)), a lipofection method (Feigner, P. L. et al., Proc. Natl. Acad. Sci. U.S.A. 84, 7413-7417 (1984)), a microinjection method (Graessmann, M.& Graessmann, A., Proc. Natl. Acad. Sci. U.S.A. 73, 366-370 (1976)), a Hanahan method (Hanahan, D., J. Mol. Biol. 166, 557-580 (1983)), a lithium acetate method (Schiestl, R. H. et al., Curr. Genet. 16, 339-346 (1989)), a protoplast-polyethylene glycol method (Yelton, M. M. et al., Proc. Natl. Acad. Sci. 81, 1470-1474 (1984)), or the like.

The transformant of the invention is capable of producing the FGDH of the invention. Therefore, the use of the transformant of the invention enables efficient production of the FGDH of the invention.

5. Method for Producing Flavin-Binding Glucose Dehydrogenase

The FGDH of the invention is produced by culturing microorganisms that are capable of producing the FGDH of the invention. Microorganisms to be cultured are not particularly limited, as long as they are capable of producing the FGDH of the invention. For example, wild-type microorganisms belonging to the genus *Circinella* mentioned in Section 1 above, and the transformants described in Section 4 above are preferably used.

Specific examples of microorganisms of the genus *Circinella* include *Circinella minor* NBRC6448, *Circinella mucoroides* NBRC4453, *Circinella muscae* NBRC6410, *Circinella rigida* NBRC6411, *Circinella simplex* NBRC6412, *Circinella umbellata* NBRC4452, *Circinella umbellata* NBRC5842, *Circinella* RD055423, and *Circinella* RD055422.

The microorganisms of the genus *Circinella* are maintained in the Biotechnology Center of the National Institute of Technology and Evaluation, and can be obtained after completing predetermined procedures.

The culture method and culture conditions are not limited, as long as the FGDH of the invention is produced. Specifically, as long as FGDH is produced, any method and conditions can be used that are suitable for the growth of the microorganisms to be used. Examples of culture conditions, such as culture medium, culture temperature, and culture period, are described below.

There is no limitation on culture media as long as the microorganisms to be used can grow. Examples include those containing carbon sources such as glucose, sucrose, gentiobiose, soluble starch, glycerin, dextrin, molasses, and organic acids, and further containing ammonium sulfate, ammonium carbonate, ammonium phosphate, and ammonium acetate; and those containing nitrogen sources, such as peptone, yeast extract, corn steep liquor, casein hydrolysate, wheat bran, meat extract, and those containing inorganic salts, such as potassium salts, magnesium salts, sodium salts, phosphoric salts, manganese salts, iron salts, and zinc salts. To promote the growth of the microorganisms, it is also possible to add vitamins, amino acids, etc., to media.

When the FGDH of the invention is obtained by culturing the microorganisms of the genus *Circinella*, the culture conditions may be selected in consideration of nutritional and physiological properties of the microorganisms. Liquid culture is performed in many cases. Industrially, it is advantageous to perform aeration-agitation culture. In terms of the productivity, however, performing solid culture may be more advantageous.

The medium has a pH of, for example, about 3 to 8, and preferably about 5 to 7. Culture is performed at a culture temperature of usually about 10 to 50° C., preferably about 25 to 35° C., for 1 to 15 days, preferably about 3 to 7 days, under aerobic conditions. As a culture method, for example, shake culture or aerobic submerged culture using a jar fermentor may be used.

It is preferable that the FGDH is recovered from the culture medium or cells after culture under the above conditions. When microorganisms that secrete FGDH out of the cells are used, the enzyme of the invention can be obtained, for example, in the following manner. Specifically, the culture supernatant is filtered, centrifuged, etc., to remove insoluble matter, and separation and purification are performed by suitably combining the following: ultrafiltration membrane concentration, ammonium sulfate precipitation and other salting out, dialysis, various chromatographies, and the like. A flavin-binding glucose dehydrogenase produced by microorganisms that belong to the genus *Circinella* is basically a secretory protein.

In contrast, when the FGDH is recovered from inside the cells, the enzyme of the invention can be obtained, for example, in the following manner. Specifically, the cells are disrupted by pressure treatment, ultrasonic treatment, mechanical technique, or techniques using enzymes such as lysozyme, and a surfactant and a chelating agent such as EDTA are optionally added to solubilize GDH, which is separated and collected as an aqueous solution, followed by separation and purification. It is also possible to perform this series of processes (cell disruption, separation, and purification) after recovering cells in advance from culture medium by filtration, centrifugation, or the like.

Purification may be performed, for example, by suitably combining vacuum concentration, membrane concentration, salting out with ammonium sulfate or sodium sulfate, fractional precipitation with a hydrophilic organic solvent such as methanol, ethanol, or acetone, heat treatment, isoelectric focusing, gel filtration with an adsorbent or a gel filtration agent, adsorption chromatography, ion-exchange chromatography, affinity chromatography, and the like.

When column chromatography is used, for example, gel-filtration column chromatography using Sephadex gel (produced by GE Healthcare Bioscience) and column chromatography using DEAF Sepharose CL-6B (produced by GE Healthcare Bioscience) or Octyl Sepharose CL-6B (produced by GE Healthcare Bioscience) may be used. It is preferable that the purified enzyme preparation be purified to the extent that the enzyme migrates as a single band on electrophoresis (SDS-PAGE).

In harvesting (e.g., extracting or purifying) a protein having glucose dehydrogenase activity from culture medium, any of the following may be used, singly or multiply, as indices: glucose dehydrogenase activity, action on maltose, thermal stability, and the like. In each purification process, in principle, the FGDH activity is used as an index for fractionation, thereby proceeding to the next step. This does not apply, however, if the appropriate conditions can be set in advance such as by performing a preliminary test.

To obtain the FGDH of the invention as a purified preparation, purification is preferably performed to the extent that the specific activity is, for example, 300 to 510 (U/mg), and preferably 400 to 510 (U/mg). The final form may either be a liquid or a solid (including a powder).

To obtain the enzyme of the invention as a recombinant protein, various modifications can be made. For example, DNA encoding the enzyme of the invention and other appropriate DNA are inserted into the same vector, which is used to produce a recombinant protein. In this manner, the enzyme of the invention made of a recombinant protein in which arbitrary peptides or proteins are linked together can be obtained. It is also possible to add sugar chains and/or lipid, or to make modifications that cause processing at the N-terminus or C-terminus. These modifications enable simplifying the extraction and purification of recombinant proteins, as well as addition of biological functions, and the like.

6. Method for Measuring Glucose

Methods for measuring glucose using glucose dehydrogenase have already been established in this technical field. The amount or concentration of glucose in various samples can be measured using the FGDH of the invention according to known methods. The mode for the measurement is not limited, as long as the FGDH of the invention is used to measure the amount or concentration of glucose. For example, the measurement may be performed by causing the FGDH of the invention to act on glucose in a sample, and spectrophotometrically measuring the structural change of the electron acceptor (e.g., DCPIP) associated with glucose dehydrogenation. More specifically, the measurement may be performed according to the method described in Section 1-1 above. According to the present invention, the glucose concentration can be measured by adding the FGDH of the invention to a sample, or by adding the FGDH of the invention to a sample, followed by mixing. The sample containing glucose is not limited. Examples of the samples include blood, beverages, foods, and the like.

The glucose concentration can be measured using a sensor described later, for example, in the following manner. A buffer solution is placed in a thermostated cell, and the temperature is maintained constant. Potassium ferricyanide, phenazine methosulfate, or the like, can be used as a mediator. An electrode on which the FGDH of the invention is immobilized is used as a working electrode, and a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

7. Glucose Assay Kit

The glucose assay kit of the invention contains the FGDH of the invention in an amount sufficient for at least one assay. In addition to the FGDH of the invention, the kit typically contains a buffer solution and a mediator required for the assay, a glucose standard solution for preparing a calibration curve, and instructions for use. The FGDH of the invention may be provided in various forms, such as a freeze-dried reagent or a solution in an appropriate storage solution.

8. Glucose Sensor

The present invention is also characterized by a glucose sensor using the FGDH of the invention. A carbon electrode, a gold electrode, a platinum electrode, or the like, is used as an electrode on which the enzyme of the invention is immobilized. Examples of methods for immobilization include a method using a crosslinking reagent, a method for encapsulating the FGDH in a polymer matrix, a method for covering the FGDH with a dialysis membrane, and methods using a photo-crosslinkable polymer, a conductive polymer, a redox polymer, or the like. Alternatively, the FGDH of the invention may be immobilized in a polymer or immobilized adsorptively onto an electrode, together with an electron mediator, such as ferrocene or its derivatives. These methods may also be used in combination. Typically, the FGDH of the invention is immobilized on a carbon electrode using glutaraldehyde, followed by treatment with an amine-containing reagent to block the glutaraldehyde.

The glucose concentration can be measured in the following manner. A buffer solution is placed in a thermostated cell, and the temperature is maintained constant. Potassium ferricyanide, phenazine methosulfate, or the like, can be used as a mediator. An electrode on which the FGDH of the invention is immobilized is used as a working electrode, and a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

In this specification, the term "product" refers to a product that contains the flavin-binding glucose dehydrogenase of the invention and that constitutes a part or the whole of one set for a user to accomplish the usage described above.

The present invention is more specifically described below by presenting Examples.

EXAMPLES

Example 1

Reconstitution of Strain

Some strains that belong to the genus *Circinella* were obtained from the National Institute of Technology and Evaluation (an incorporated administrative agency). Ampules of L-dried strain samples were opened, and 100 µL of reconstitution water was supplied to each sample so as to suspend the dried cells in the water. Thereafter, each suspension was added to a reconstitution medium dropwise, and statically cultured at 25° C. for 3 to 7 days, thereby reconstituting the strain. Sterilized water (distilled water treated in an autoclave at 120° C. for 20 minutes) was used as reconstitution water, and DP medium (dextrin 2.0%, polypeptone 1.0%, KH$_2$PO$_4$ 1.0%, agarose 1.5%) was used as reconstitution medium. 100 µL of each strain stocked in glycerol was reconstituted by being plated on DP agar medium.

Example 2

Collection of Culture Supernatant

A loopful of each strain of the genus *Circinella* reconstituted in Example 1 was inoculated in a solid medium containing 2 g of wheat germ and 2 mL of water sterilized in an autoclave at 120° C. for 20 minutes, and was statically cultured at 25° C. for about 3 to 7 days. After the culture, 4 mL of 50 mM potassium phosphate buffer solution (pH of 6.0) containing 2 mM EDTA was added, and the cells were sufficiently suspended by vortex mixing. After a small amount of glass beads were added to the suspension, the cells were disrupted using a beads shocker (Yasui Kikai Corporation) at 3,000 rpm for 3 minutes, twice, followed by centrifugation for 5 minutes at 4° C., 2,000×g. The resulting supernatant was used as a crude enzyme solution.

Example 3

Confirmation of Glucose Dehydrogenase Activity

The activity of glucose dehydrogenase in the crude enzyme solution obtained in Example 2 was measured according to the FGDH measurement method shown in Section 1-1 above. Table 1 shows the results.

TABLE 1

| Strain | Activity (U/ml) |
|---|---|
| *Circinella minor* NBRC6448 | 0.01 |
| *Circinella mucoroides* NBRC4453 | 0.07 |
| *Circinella muscae* NBRC6410 | 0.04 |
| *Circinella rigida* NBRC6411 | 0.02 |
| *Circinella simplex* NBRC6412 | 0.46 |
| *Circinella umbellata* NBRC4452 | 0.03 |
| *Circinella umbellata* NBRC5842 | 0.02 |
| *Circinella* RD055422 | 10.7 |

The results of Table 1 show that GDH activity was confirmed in the crude enzyme solutions from *Circinella minor* NBRC6448, *Circinella mucoroides* NBRC4453, *Circinella muscae* NBRC6410, *Circinella rigida* NBRC6411, *Circinella simplex* NBRC6412, *Circinella umbellata* NBRC4452, *Circinella umbellata* NBRC5842, and *Circinella* RD055422.

Example 4

Purification of Fgdh from *Circinella simplex* Nbrc6412 and *Circinella* RD055422

50 mL of DP liquid medium was placed in a 500-mL Sakaguchi flask and sterilized in an autoclave, thereby preparing a preculture medium. A loopful of *Circinella simplex* NBRC6412 and a loopful of *Circinella* RD055422, both reconstituted in advance in DP plate medium, were separately inoculated in the preculture medium and subjected to shaking culture for 3 days at 25° C., 180 rpm, thereby obtaining a seed culture solution.

Next, 6.0 L of a production medium (yeast extract 2.0%, glucose 1%, pH of 6.0) was placed in a 10-L jar fermenter and sterilized in an autoclave, thereby obtaining a main culture medium. 50 mL of the seed culture solution was inoculated in the main culture medium and was cultured for 3 days under the following conditions: culture temperature=25° C., stirring speed=600 rpm, air flow rate=2.0 L/min, and tube internal pressure=0.2 MPa. Thereafter, the culture solution was filtrated with a filter cloth, thereby collecting fungal cells. The resulting cells were suspended in a 50 mM potassium phosphate buffer solution (pH of 6.0).

The suspension was supplied to a French press (Niro Soavi) at a flow rate of 160 mL/min, and the cells were disrupted at 1,000 to 1,300 bar. Subsequently, ammonium sulfate (Sumitomo Chemical Co., Ltd.) was gradually added to the disrupted cell solution to give 0.2 saturation, and was stirred at room temperature for 30 minutes. Extra precipitates were removed using a filtration adjuvant. Then, the solution was concentrated using a UF membrane (Millipore) having a molecular weight cutoff of 10,000, and the concentrated solution was desalinated using Sephadex G-25 gel. Thereafter, ammonium sulfate was gradually added to the desalinated liquid to give 0.5 saturation, and the resulting liquid was subjected to linear gradient elution with 50 mM phosphate buffer solution (pH of 6.0) by being passed through a 400-mL SP Sepharose Fast Flow column (GE Healthcare) equilibrated in advance with 50 mM potassium phosphate buffer solution (pH of 6.0) containing 0.5-saturated ammonium sulfate. Thereafter, the eluted GDH fraction was concentrated using a hollow fiber membrane (Spectrum Laboratories, Inc.) having a molecular weight cutoff of 10,000, and passed through a DEAE Sepharose Fast Flow column (GE Healthcare), thereby obtaining a purified enzyme. The resulting purified enzyme was subjected to SDS-polyacrylamide gel electrophoresis (PhastGel 10-15% PhastSystem: GE Healthcare). Phosphorylase b (97,400 Da), bovine blood serum albumin (66,267 Da), aldolase (42,400 Da), carbonic anhydrase (30,000 Da), and trypsin inhibitor (20,100 Da) were used as protein molecular weight markers. FIG. 1 shows the results for *Circinella simplex* NBRC6412.

As shown in FIG. 1, the presence of a single band showed that FGDH from *Circinella simplex* NBRC6412 was fully purified. Further, the mobility compared with the molecular weight markers showed that the molecular weight of FGDH from *Circinella simplex* NBRC6412 was 90,000 to 110,000 Da.

Example 5

Molecular Weight of Peptide Moiety of Isolated FGDH

Figure 2:
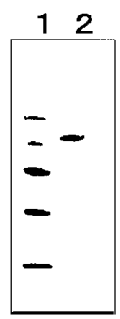
FIG. 2 shows the results of SDS-PAGE of *Circinella simplex* NBRC6412-derived FGDH deglycosylated with F-glycosidase.

The purified *Circinella simplex* NBRC6412-derived FGDH obtained in Example 4 was denatured by heating at 100° C. for 10 minutes, and then treated with 5 U of N-Glycosidase F (Roche Diagnostics.jp) at 37° C. for an hour, thereby decomposing the sugar chain added to the protein. Thereafter, the same measurement as in Example 4 was performed using SDS-polyacrylamide gels electrophoresis. The same molecular weight markers as in Example 4 were used (FIG. 2). The results shown in FIG. 2 revealed that the molecular weight of the polypeptide moiety of the purified FGDH was about 70,000 Da. As described later, the molecular weight of FGDH from *Circinella* RD055422 is also about 70,000 Da, since FGDH from *Circinella* RD055422 has only 1 amino acid difference from that of FGDH from *Circinella* simplex NBRC6412.

Example 6

Substrate Specificity

According to the above method for measuring the activity of FGDH, substrate specificity of the purified enzyme was evaluated by comparing the activity with respect to D-glucose as a substrate and the apparent activity with respect to sugar (control). Maltose, D-galactose, and D-xylose were used as the sugar as a control. The concentration of each substrate was 50 mM. Table 2 shows the results.

TABLE 2

|  | Relative Activity (%) | |
| --- | --- | --- |
|  | Circinella simplex NBRC6412 | Circinella RD055422 |
| D-Glucose | 100 | 100 |
| Maltose | 0.6 | 0.6 |
| D-Galactose | 0.4 | 1.9 |
| D-Xylose | 1.2 | 1.1 |

The results of Table 2 revealed that the apparent activities of FGDH with respect to maltose, D-galactose, and D-xylose were all 2% or less, relative to its activity with respect to D-glucose (100%). It was thus shown that FGDH of the present invention has excellent substrate specificity.

Example 7

Optimal Activity pH

Figures 1, 3:
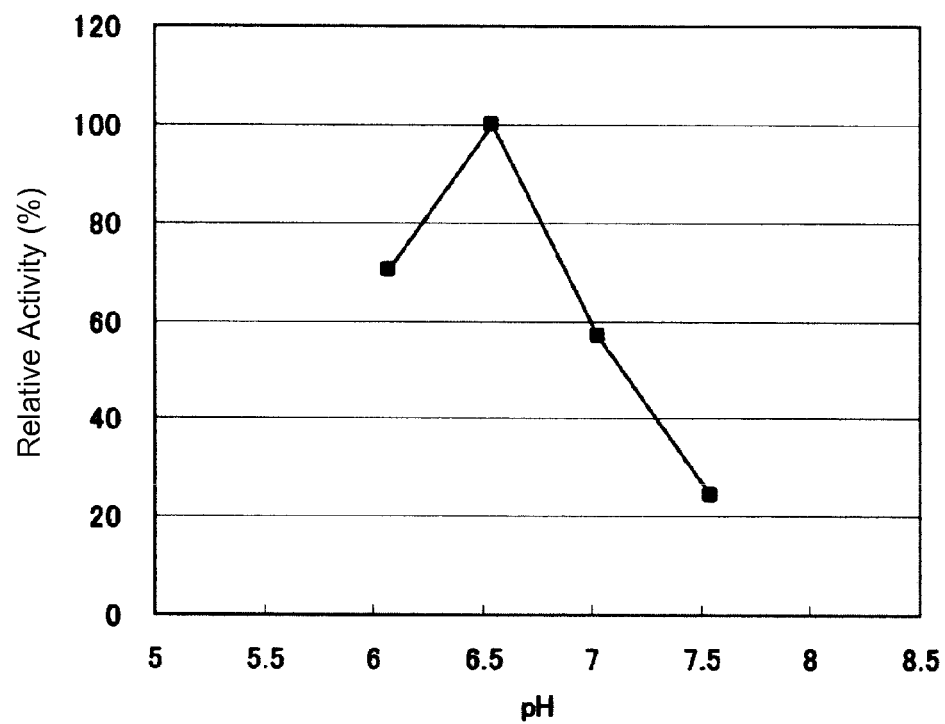
Figures 2, 3:
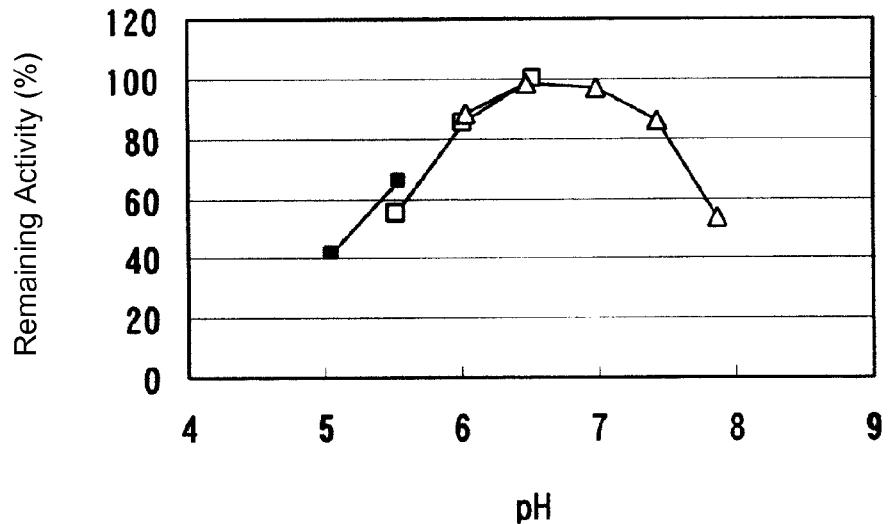

The optimal pH was found using the FGDH enzyme liquid (100 U/mL) obtained in Example 4. The optimal pH of FGDH from *Circinella simplex* NBRC6412 was measured using a 50 mM PIPES-NaOH buffer solution (pH of 6.0 to 7.5) as a buffer solution. The optimal pH of FGDH from *Circinella* RD055422 was measured using 50 mM potassium acetate (pH of 5 to 5.5), MES-NaOH (pH of 5.5 to 6.5), and potassium phosphate (pH of 6.0 to 8.0) as buffer solutions. FIG. 3-1 (NBRC6412) and FIG. 3-2 (RD055422) show the results.

As shown in the figures, it was revealed that the FGDH of the present invention showed the highest apparent activity at a pH of 6.5. Since the activity at a pH of 6.5 is higher than the activities at a pH of 6.0 and 7.0, it was revealed that the optimal pH is around 6.5.

Example 8

Optimal Activity Temperature

Figures 1, 4:
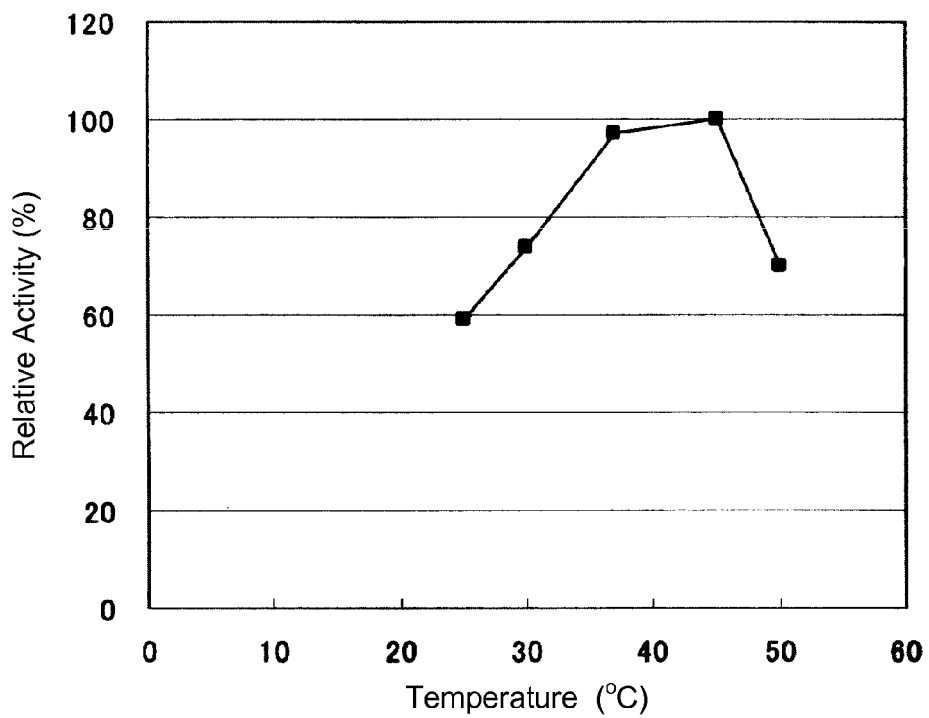
Figures 2, 4:
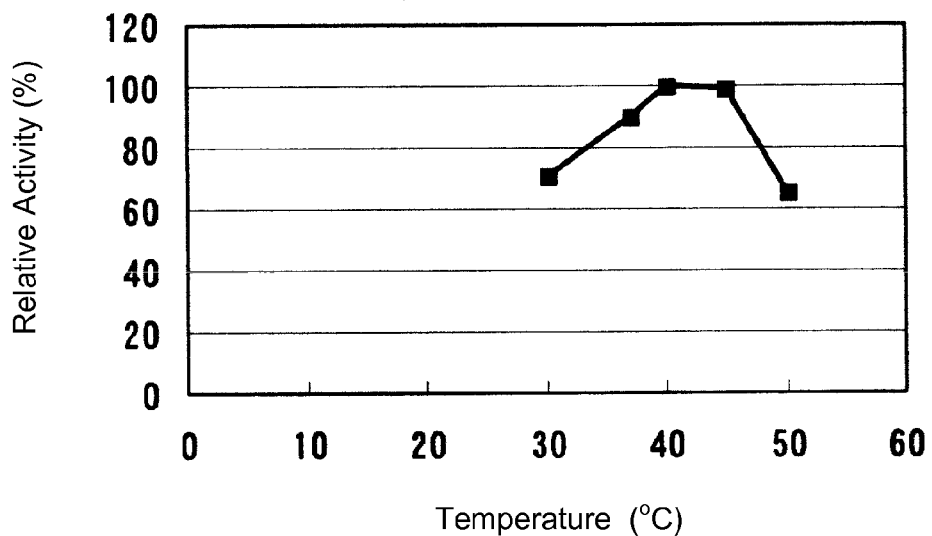

The optimal temperature was found using the FGDH enzyme liquid (0.1 U/mL) obtained in Example 4. The apparent activities at 25° C., 30° C., 37° C., 40° C., 45° C., and 50° C. were measured using a 42 mM PIPES-NaOH buffer solution (pH of 6.5) as a buffer solution. FIGS. 4-1 (NBRC6412) and 4-2 (RD055422) show the results.

As shown in the figures, the apparent activity of FGDH of the present invention was the highest at a temperature range of 37° C. to 45° C., among the activities measured at 25° C., 30° C., 37° C., 40° C., 45° C., and 50° C. The activity at 45° C. was higher than the activity at 50° C. Thus it was revealed that the optimal temperature is about 37° C. to 45° C.

Example 9 pH Stability

Figures 1, 5:
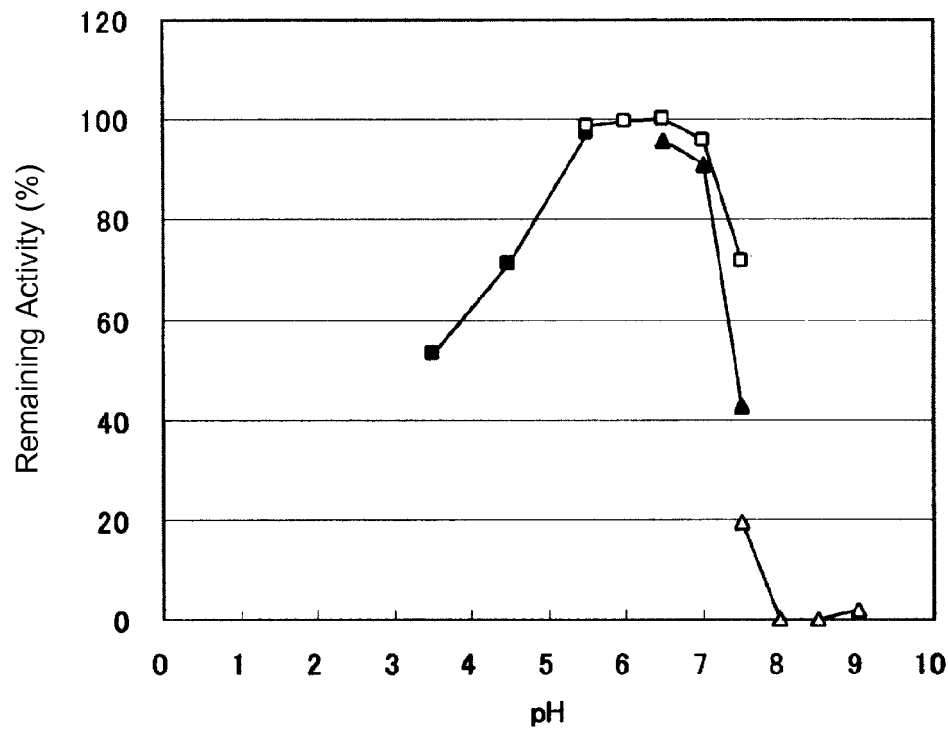
Figures 2, 5:
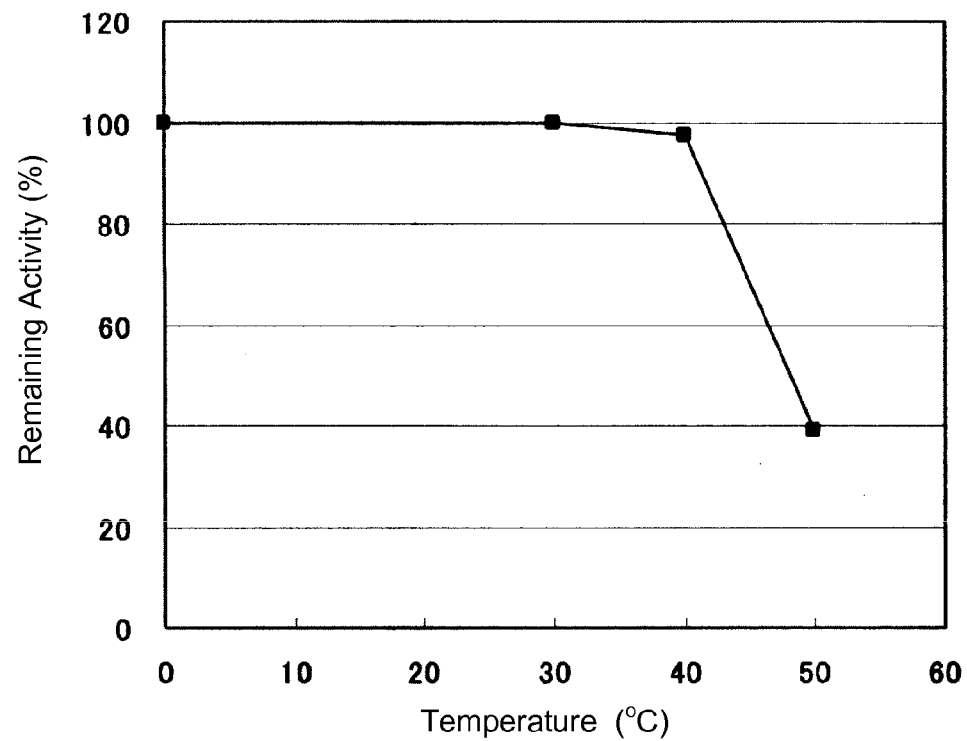

The pH stability was measured using the FGDH enzyme liquid (10 U/mL) obtained in Example 4. After treated with 100 mM acetic acid-sodium buffer solution (pH of 3.0 to 5.5, plotted with black squares in the figure), 100 mM phosphoric acid-potassium buffer solution (pH of 5.5 to 7.5, plotted with white squares in the figure), 100 mM tris-HCl buffer solution (pH of 7.5 to 9.0, plotted with white triangles in the figure), and 100 mM PIPES-NaOH buffer solution (pH of 6.5 to 7.5, plotted with black triangles in the figure) for 16 hours at 25° C., the apparent remaining activity of the enzyme liquid was measured. FIGS. 5-1 (NBRC6412) and 5-2 (RD055422) show the results.

The results revealed that, based on a pH of 6.5 where the apparent remaining activity becomes maximum (100%), the pH value at which the remaining activity (relative value) was 80% or more was a pH of 5.3 to 7.2 for NBRC6412-derived FGDH, and a pH of 3.5 to 8.0 for RD055422-derived FGDH.

Example 10

Thermal Stability

Figures 1, 6:
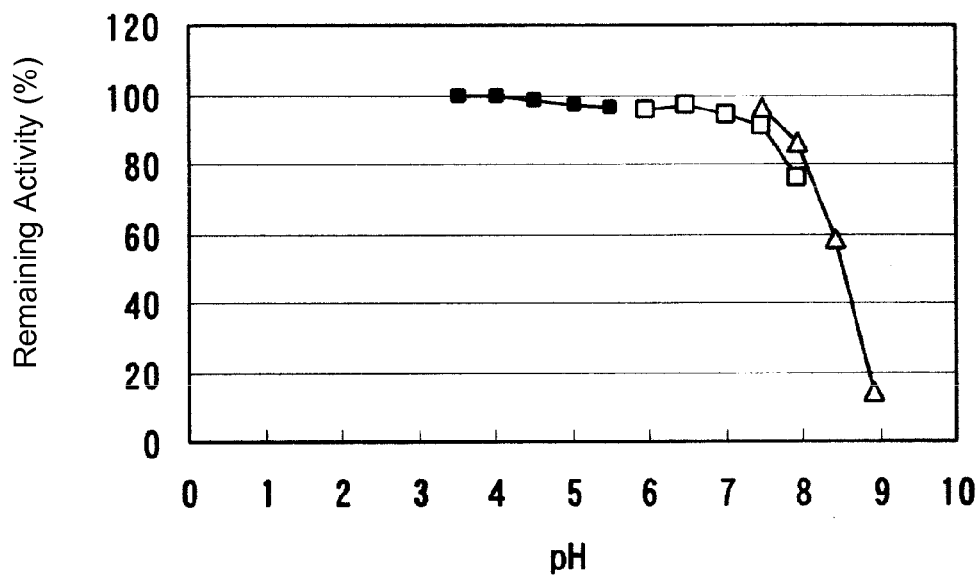
Figures 2, 6:
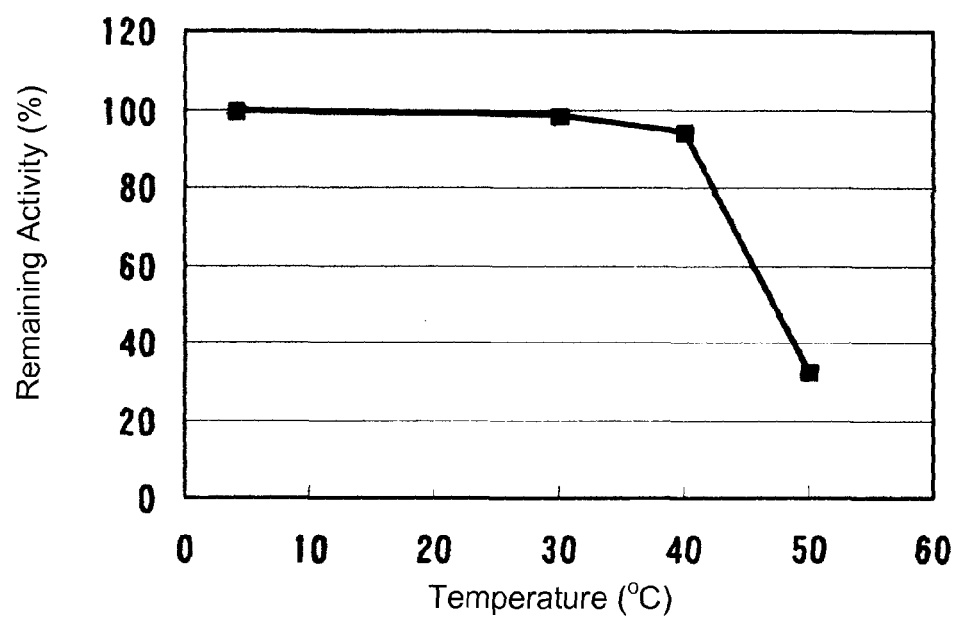

The thermal stability was measured using the FGDH enzyme liquid (10 U/mL) obtained in Example 4. The FGDH enzyme liquid was treated with 100 mM potassium acetate buffer solution (pH of 5.0) for 15 minutes at different temperatures (4° C., 30° C., 40° C., and 50° C.); thereafter, apparent remaining activities were measured. FIGS. 6-1 (NBRC6412) and 6-2 (RD055422) show the results.

The results revealed that the remaining activity of the FGDH of the present invention was 98% for NBRC6412 and 94% for RD055422 at 40° C. This showed that the FGDH is stable at a temperature of 40° C. or less.

Example 11

Measurement of Km Value

Figures 1, 7:
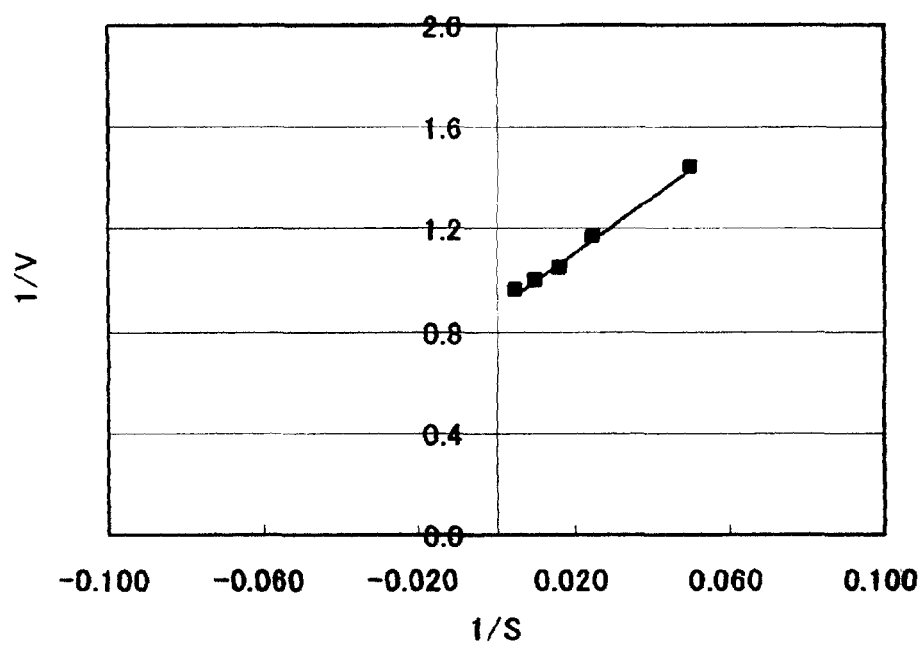
Figures 2, 7:
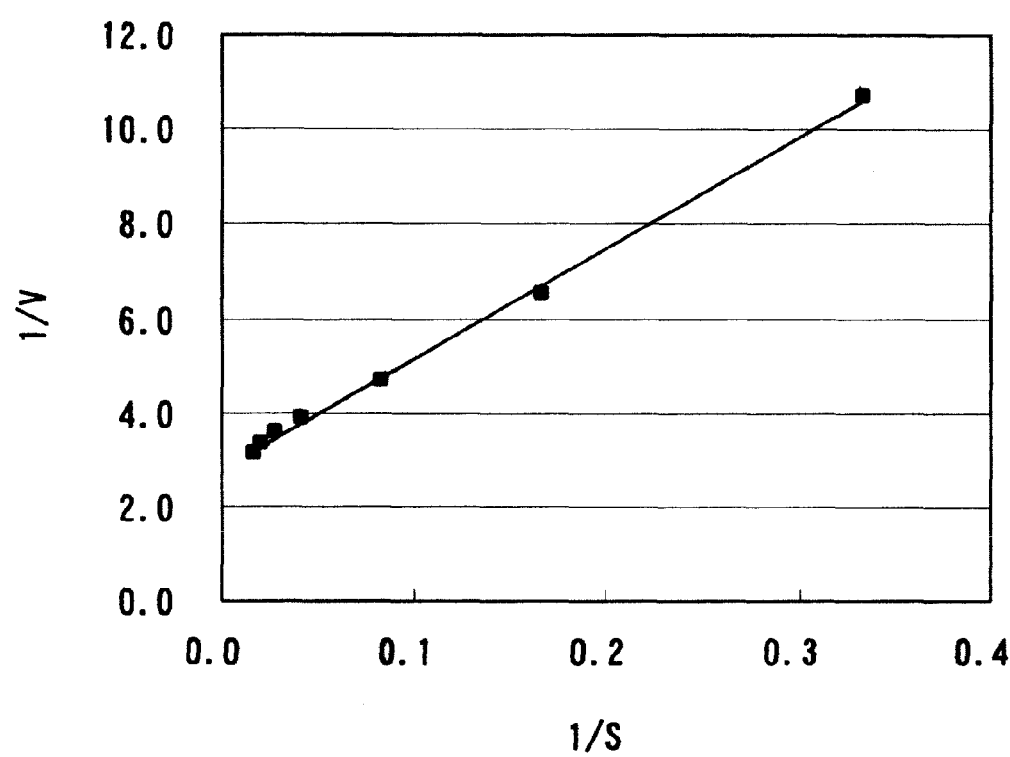

The apparent activity was measured by changing the concentration of D-glucose (substrate) using the FGDH activity measurement method described above, thereby creating a Lineweaver-Burk plot (FIG. 7-1 (NBRC6412) and FIG. 7-2 (RD055422)) to find the Km values. The Km value of the FGDH of the present invention with respect to D-glucose was 12.5 mM for NBRC6412 and 8.3 mM for RD055422.

Example 12

Isolation of DNA Encoding FGDH (1) Extraction of Chromosomal DNA

*Circinella simplex* NBRC6412 was cultured overnight at 25° C. in a Sakaguchi flask containing 50 ml of YG culture medium (yeast extract 1%, glucose 2%). Thereafter, the culture solution was filtered using a Buchner funnel and a Nutsche suction bottle, thereby obtaining fungal cells. Among the obtained cells, about 0.3 g was frozen in liquid nitrogen, and the hypha was pulverized using a mortar and suspended in 12 ml of an extraction buffer (containing 1% hexadecyltrimethylammonium bromide, 0.7 M NaCl, 50 mM Tris-HCl (pH of 8.0), 10 mM EDTA, and 1% mercapto ethanol). After the suspension was stirred at room temperature for 30 minutes, the equivalent amount of a solution containing phenol:chloroform:isoamyl alcohol (25:24:1) was added. The mixture was stirred and centrifuged (1,500 g, 5 minutes, room temperature), thereby obtaining a supernatant. The equivalent amount of a solution containing chloroform:isoamyl alcohol (24:1) was added to the resulting supernatant, and the mixture was centrifuged (1,500 g, 5 minutes, room temperature). The equivalent amount of isopropanol was added to the resulting supernatant. The resulting precipitate of chromosomal DNA was centrifuged (20,000 g, 10 minutes, 4° C.), and the precipitate resulting from the centrifugation was washed with 70% ethanol and was vacuum-dried.

The chromosomal DNA thus obtained was again dissolved in 4 ml of TE, and 200 μL of 10 mg/ml RNase A (Sigma-Aldrich Japan K.K.) was added, followed by incubation at 37° C. for 30 minutes. Then, after 40 μL of 20 mg/ml solution containing Proteinase K, recombinant, PCR Grade (Roche Diagnostics.jp) was added, the mixture was incubated for 30 minutes at 37° C., and the equivalent amount of a solution containing phenol:chloroform:isoamyl alcohol (25:24:1) was added. After stirring, centrifugation (1,500 g, 5 minutes, room temperature) was performed to obtain a supernatant. After the same washing was performed twice, the equivalent amount of a solution containing chloroform:isoamyl alcohol (24:1) was added to the resulting supernatant and stirred, followed by centrifugation (1,500 g, 5 minutes, room temperature). The resulting supernatant was mixed with 3 M NaOAc (pH of 4.8) (1/10 volume of the supernatant) and ethanol (2.5 times the supernatant), and the liquid was centrifuged (20,000 g, 20 minutes, 4° C.), thereby collecting chromosomal DNA. The collected chromosomal DNA was washed with 70% ethanol, vacuum-dried, and finally dissolved in 400 μL TE solution, thereby obtaining a chromosomal DNA solution having a concentration of about 1 mg/ml.

(2) Design of Synthetic Primer

With reference to amino acid sequence of *Aspergillus oryzae*-derived GDH represented by SEQ ID NO: 3 (corresponding to the amino acid sequence of SEQ ID NO: 4 in the sequence listing in U.S. Pat. No. 4,292,486) or other known amino sequences, degenerate primers degeF11 and degeR13 (SEQ ID NOS: 4 and 5) containing mixed bases were synthesized with respect to regions where amino acid sequences are presumably relatively conserved.

(3) Acquisition of Partial Sequence of FGDH Gene by PCR

Using the chromosomal DNA thus obtained in Section (1) above as a template, PCR was performed using DNA polymerase KOD-Plus (Toyobo Co., Ltd.) under recommended conditions. The primers (SEQ ID NOS: 4 and 5) obtained in Section (2) above were used as the primer. The PCR reaction mixture was subjected to agarose gel electrophoresis, and a band of about 1500 bp was confirmed. The amplified DNA fragment was purified and cloned into vector pTA2 using a cloning kit Target Clone-Plus (Toyobo Co., Ltd.) according to the protocol, thereby being introduced into *Escherichia coli* DH5α-strain competent cells (Toyobo Co., Ltd.) to obtain a transformant.

The transformant was cultured in LB culture medium, and plasmids were extracted. Then, the base sequence of the region corresponding to the enzyme gene was analyzed. The sequence reaction was performed using a BigDye™ Terminator v3.1 Cycle Sequencing Kit (Applied Biosystems Japan), according to the user's manual of the product. The analysis was performed using an ABI PRISM 310 sequencer (Applied Biosystems Japan). The base sequence analysis of the enzyme gene was performed using a sequence analyzing primer, and the primers mentioned above (SEQ ID NOS: 4 and 5), P7 (SEQ ID NO: 6), and P8 (SEQ ID NO: 7). As a result of the base sequence analysis, a partial sequence of FGDH of about 1500 bp was obtained.

(4) Acquisition of Entire Sequence of FGDH Gene

Based on the base sequence thus obtained, two new primers (SEQ ID NOS: 8 and 9) directed outward from the gene were designed so as to obtain the gene sequence in the N-terminal direction including a start codon. With these inverse PCR primers, inverse PCR was performed using DNA polymerase KOD-Plus (Toyobo Co., Ltd.) under recommended conditions, using, as a template, the chromosomal DNA obtained in Section (1) above treated with restriction enzyme HindIII and ligated. The sequence of the amplified fragment was analyzed in the same manner as above, thereby clarifying the upstream base sequence including a sequence assumed to be a start codon. Further, to obtain the gene sequence in the C-terminal direction including a stop codon, inverse PCR was performed in the same manner as above with the above inverse PCR primers (SEQ ID NOS: 10 and 11), using, as a template, the genomic DNA obtained in Section (1) above treated with restriction enzyme EcoRI and ligated. The sequence of the amplified fragment was analyzed in the same manner as above, thereby clarifying the upstream base sequence including a sequence assumed to be a stop codon.

(5) Determination of N-Terminus and C-Terminus

Using known information to the greatest possible extent, the N-terminus was determined through multilateral comparison with the sequence obtained in Section (4) above in view of homology of amino acid sequences, lengths of base sequences, etc., thereby identifying a start codon. The C-terminus was determined in the same manner.

(6) Design of Primers for Amplifying Entire Length of GDH Gene from *Circinella simplex*

Based on the determination in Section (5) above, a primer 5UTR F1 (SEQ ID NO: 12) annealing upstream of the start codon, and a primer 3UTR R1 (SEQ ID NO: 13) annealing downstream of the stop codon were designed.

(7) Determination of cDNA Sequence

*Circinella simplex* NBRC6412 (yeast extract 1%, glucose 2%) was cultured overnight in a 50-ml YG culture medium in a Sakaguchi flask at 25° C. Thereafter, the culture solution was filtered using a Buchner funnel and a Nutsche suction bottle, thereby obtaining fungal cells. Among the obtained cells, about 0.3 g was frozen in liquid nitrogen, and the hypha was pulverized using a mortar. Then, using ISOGEN (Nippon Gene Co., Ltd.), mRNA was obtained from the pulverized cells according to the protocol of the kit. Using this as a template, reverse transcription was performed using ReverTra-Ace (Toyobo Co., Ltd.) according to the protocol, thereby synthesizing cDNA. 3UTR R1 (SEQ ID NO: 13) obtained in Section (6) above was used as a primer for the reverse transcription. Then, using the synthesized cDNA as a template, PCR was performed using DNA polymerase KOD-Plus (Toyobo Co., Ltd.) under recommended conditions. The PCR was performed using the primers (SEQ ID NOS: 12 and 13) obtained in Section (6) above. The PCR reaction mixture was subjected to agarose gel electrophoresis. As a result, a band of about 2050 bp was confirmed. The sequence analysis of the amplified DNA fragment was performed in the same manner as above. In this cDNA sequence analysis, the base sequences of plasmids from three different clones were analyzed. Primers for sequence analysis (SEQ ID NOS: 14 and 15) were also used in the base sequence analysis. In this manner, the cDNA sequence of FGDH from *Circinella simplex* NBRC6412 was determined (SEQ ID NO: 2). The amino acid sequence of the enzyme gene encoded by the cDNA sequence is shown in SEQ ID NO: 1.

(8) Determination of DNA and Amino Acid Sequence of FGDH Derived from RD055422

The same procedure as in Sections (1) to (7) above was performed using *Circinella* RD055422 strain, thereby determining amino acid sequences (SEQ ID NO: 16) and cDNA sequence (SEQ ID NO: 17) of FGDH from RD055422 strain.

(9) Comparison with Known GDH in Terms of Amino Acid Sequence

The identities of the amino acid sequence found in Section (7) above with known FADGDH from *Aspergillus oryzae* and FADGDH from *Aspergillus terreus* were 35% and 34%, respectively. The calculation in the amino acid sequence analysis was performed using a default parameter of the homology algorithm BLAST (Basic Local Alignment Search Tool: www.ncbi.nlm.nih.gov/BLAST/) of the National Center for Biotechnology Information (NCBI).

Example 13

Confirmation of Expression and Enzymatic Activity of FGDH from *Circinella simplex* NBRC6412 and FGDH from *Circinella* RD055422 in *Saccharomyces cerevisiae*

(1) Construction of Expression Vector

Using a recombinant plasmid pCSGDH containing FGDH gene (SEQ ID NO: 2) from *Circinella simplex* or FGDH gene (SEQ ID NO: 17) from *Circinella* RD055422 strain found in Example 12 as a template, a DNA fragment including an open reading frame was amplified using primers (SEQ ID NOS: 18 and 19) in which the N-terminus and C-terminus are respectively bonded to cleavage sites of restriction enzymes BamHI and XhoI. This DNA fragment was cleaved by the restriction enzymes BamHI and XhoI, and mixed with a vector plasmid pYES3 (Invitrogen) cleaved by the same enzymes. The equivalent amount of a ligation reagent (Ligation high: Toyobo Co., Ltd.) was added to the mixed solvent, and the resulting mixture was incubated for ligation. The thus-ligated DNA was introduced into *Escherichia coli* DH5α strain competent cells (Competent High DH5α: Toyobo Co., Ltd.) according to the protocol included, thereby obtaining a transformant. The transformant was cultured in LB medium, thereby extracting a plasmid. In this manner, an expression vector capable of mass expression in *Saccharomyces cerevisiae* was constructed.

(2) Transformation

Thereafter, *Saccharomyces cerevisiae* INVSc1 (Invitrogen) was also transformed with the DNA according to the instructions for pYES3.

(3) Culture

The resulting transformant was cultured using a 10-L jar fermenter (BMS10-PI: Biott Corporation). The seed culture was performed according to the instructions, and the main culture was performed in a medium containing 3% yeast extract, 1% polypeptone, and 3% galactose (medium liquid amount=6.0 L, stirring speed=400 rpm, temperature=25° C., air flow rate=1.0 vvm). Then, the GDH activity of the crude enzyme solution thus obtained was confirmed. The results confirmed expression of FGDH of the present invention.

This invention is not limited to the above Embodiments and Examples. The invention also includes variations and modifications within the scope of the patent claims set forth below and within a range readily conceived of by those skilled in the art.

The entire content of papers, laid-open patent applications, and patent publications referred to in this specification is incorporated herein by reference.

INDUSTRIAL APPLICABILITY

The FGDH of the invention has excellent substrate specificity, and is capable of more accurately measuring the amount of glucose. The FGDH of the invention is thus suitable, for example, for measuring blood glucose levels.

The invention claimed is:

1. An electrode comprising a flavin-binding glucose dehydrogenase comprising a polypeptide having an amino acid sequence with 90% or more identity to the amino acid sequence of SEQ ID NO: 1, and having glucose dehydrogenase activity, wherein the flavin-binding glucose dehydrogenase is immobilized onto the electrode.

2. The electrode of claim 1, wherein the polypeptide has an amino acid sequence with 95% or more identity to the amino acid sequence of SEQ ID NO: 1.

3. The electrode of claim 1, wherein the polypeptide has an amino acid sequence with 98% or more identity to the amino acid sequence of SEQ ID NO: 1.

4. The electrode of claim 1, wherein the flavin-binding glucose dehydrogenase further has at least one of the following characteristics (1) to (8):

(1) Molecular weight: the molecular weight of a polypeptide moiety in the enzyme is about 70 kDa as measured by SDS-polyacrylamide electrophoresis;
(2) Km value: the Km value for D-glucose is about 20 mM or less;
(3) Substrate specificity: the reactivity to D-xylose is 1.7% or less, based on the reactivity to D-glucose taken as 100%;
(4) Optimal activity temperature: 37 to 45° C.;
(5) Optimal activity pH: 6.5;
(6) pH stability: stable at a pH range of 5 to 7;
(7) Temperature stability: stable at a temperature of 40° C. or less; and
(8) Origin: the enzyme is derived from microorganisms of the genus *Circinella*.

5. A sensor comprising the electrode of claim 1.

* * * * *

SEQUENCE LISTING

```
<160> NUMBER OF SEQ ID NOS: 19

<210> SEQ ID NO 1
<211> LENGTH: 637
<212> TYPE: PRT
<213> ORGANISM: Circinella simplex

<400> SEQUENCE: 1

Met Lys Ile Ser Ala Ala Val Val Thr Ile Val Thr Ala Phe Ala Ser
1               5                   10                  15

Val Ala Thr Ala Gln Gln Gln Asn Thr Ser Glu Thr Asn Thr Tyr Asp
            20                  25                  30

Tyr Val Ile Val Gly Gly Gly Val Gly Gly Leu Ala Leu Ala Ser Arg
        35                  40                  45

Leu Ser Glu Asn Lys Gly Val Ser Val Ala Val Leu Glu Ala Gly Pro
    50                  55                  60

Tyr Ala Gly Asp Gln Phe Val Val Tyr Ala Pro Gly Met Tyr Gly Gln
65                  70                  75                  80

Ala Val Gly Thr Asp Leu Cys Pro Leu Leu Pro Thr Thr Pro Gln Glu
```

```
                    85                  90                  95
Asn Met Gly Asn Arg Ser Leu Ser Ile Ala Thr Gly Lys Leu Leu Gly
            100                 105                 110
Gly Gly Ser Ser Val Asn Gly Leu Val Trp Thr Arg Gly Gly Leu Lys
            115                 120                 125
Asp Phe Asp Ala Trp Glu Glu Leu Gly Asn Pro Gly Trp Asn Gly Ala
130                 135                 140
Ser Met Phe Asn Tyr Phe Lys Lys Val Glu Asn Phe Thr Pro Pro Thr
145                 150                 155                 160
Pro Ala Gln Ala Ala Tyr Gly Ala Thr Tyr Gln Lys Asn Ala His Gly
                165                 170                 175
Thr Lys Gly Pro Met Asp Val Ser Phe Thr Asn Phe Glu Phe Pro Gln
                180                 185                 190
Ser Gly Asn Trp Asn Ala Ser Leu Asn Ala Val Gly Phe Thr Ala Val
                195                 200                 205
Pro Asp Leu Leu Asn Gly Thr Leu His Gly Tyr Ser Thr Thr Pro Asn
210                 215                 220
Ile Leu Asp Pro Val Asn Ala Arg Arg Ala Asp Ala Tyr Ala Gly Tyr
225                 230                 235                 240
Ile Lys Pro Tyr Ile Ser Arg Asn Asn Leu Ala Val Leu Ala Asn His
                245                 250                 255
Thr Val Ser Arg Ile Gln Phe Ala Pro Gln Ser Gly Ser Gln Pro Leu
                260                 265                 270
Arg Ala Thr Gly Val Glu Trp Tyr Pro Thr Gly Asp Lys Ser Gln Lys
                275                 280                 285
Gln Val Leu Asn Ala Arg Tyr Glu Val Ile Leu Ser Ser Gly Ala Ile
                290                 295                 300
Gly Ser Pro Lys Leu Leu Glu Leu Ser Gly Ile Gly Asn Lys Asp Ile
305                 310                 315                 320
Val Ala Ala Ala Gly Ile Gln Ser Leu Leu Asp Leu Pro Gly Val Gly
                325                 330                 335
Ser Asn Met Gln Asp His Val His Ala Val Thr Val Ser Thr Thr Asn
                340                 345                 350
Ile Thr Gly Tyr Thr Thr Asn Ser Ile Phe Thr Asn Asp Ala Leu Ala
                355                 360                 365
Ala Glu Glu Arg Gln Glu Tyr Asp Asn Asn Lys Thr Gly Ile Tyr Thr
                370                 375                 380
Thr Thr Pro Asn Asn Leu Gly Tyr Pro Ser Pro Ser Gln Leu Phe Arg
385                 390                 395                 400
Gly Thr Ser Phe Val Ser Gly Lys Gln Phe Ala Ala Arg Ile Arg Asn
                405                 410                 415
Thr Thr Asp Glu Trp Ala Glu Arg Tyr Ala Ala Asp Asn Ala Thr Asn
                420                 425                 430
Ala Glu Leu Leu Lys Lys Gln Tyr Ala Ile Ile Ala Ser Arg Tyr Glu
                435                 440                 445
Glu Asp Tyr Leu Ser Pro Ile Glu Ile Asn Leu Thr Pro Gly Tyr Gly
                450                 455                 460
Gly Thr Ala Asp Val Asp Leu Thr Asn Asn Lys Tyr Gln Thr Val Asn
465                 470                 475                 480
His Val Leu Ile Ala Pro Leu Ser Arg Gly Tyr Thr His Ile Lys Ser
                485                 490                 495
Ala Asp Ile Glu Asp Ala Val Asp Ile Asn Pro Gln Tyr Tyr Ser His
                500                 505                 510
```

```
Pro Met Asp Val Asp Val His Val Ala Ser Thr Lys Leu Ala Arg Glu
        515                 520                 525

Ile Ile Ser Ala Ser Pro Gly Leu Gly Asp Ile Asn Ser Gly Glu Thr
530                 535                 540

Glu Pro Gly Lys Glu Ile Thr Ser Asp Ser Asp Val Arg Lys Trp Leu
545                 550                 555                 560

Ala Asp Asn Val Arg Ser Asp Trp His Pro Val Gly Thr Cys Ala Met
                565                 570                 575

Leu Pro Lys Glu Leu Gly Gly Val Val Asp Pro Asn Leu Lys Val Tyr
            580                 585                 590

Gly Thr Ser Asn Leu Arg Val Val Asp Ala Ser Val Met Pro Leu Glu
        595                 600                 605

Val Ser Ser His Leu Met Gln Pro Thr Phe Gly Ile Ala Glu Lys Ala
    610                 615                 620

Ala Asp Ile Ile Lys Ser Ala Asn Lys Lys Arg Ser Asn
625                 630                 635

<210> SEQ ID NO 2
<211> LENGTH: 1914
<212> TYPE: DNA
<213> ORGANISM: Circinella simplex

<400> SEQUENCE: 2
atgaagatat ctgctgctgt agttactatt gttacagctt tcgcttctgt cgctacggct     60
caacagcaaa ataccagtga aactaatacc tatgactacg ttattgttgg tggtggtgta    120
ggaggtttag ctttggctag tcgtctatct gaaaacaagg gtgtttcagt tgctgtactc    180
gaagcaggtc cgtatgctgg agatcagttt gtagtttacg ctcctggcat gtatggccaa    240
gctgtgggta ctgatctctg tcctctcctt cctactactc ctcaagagaa tatggggaac    300
agaagtctta gtattgccac tggtaaattg cttggtggcg tagttctgt caatggcctt     360 gtttggacac ggggtggttt aaaagacttt gacgcttggg aagaactcgg caaccctggc    420
tggaacggtg ccagcatgtt caattacttt aaaaaggttg aaaactttac ccctcccact    480
cctgctcaag cagcatatgg tgccacttat caaaagaatg ctcatggcac aaagggtcct    540
atggatgttt cctttaccaa tttcgaattt cctcagtctg caactggaa cgcttctctc     600 aacgctgttg gctttactgc tgtccctgat ctcttaaacg gtacacttca tggttattct    660
actacaccta atattctcga tcctgtaaat gcccgtcgtg ctgatgctta cgctggctac    720
ataaaaccct acataagccg taataacctc gctgtcttgg ctaaccatac tgtttcacgt    780
attcaatttg ctccccaaag tggtagccaa cctcttcgcg ctactggtgt tgagtggtat    840
cctactggta caaatctca aaagcaagtc ttgaatgctc gctatgaagt tattctctcg    900
tctggtgcta ttggtagccc caagcttttg gagctgtctg gtattggtaa caaggacatt    960
gtcgctgccg ctggtattca atctttgctt gatttgcctg tgttggttc taatatgcaa    1020 gatcacgtac atgccgttac ggtttctacc acaaacatca ctggttacac caccaacagc    1080
atctttacca acgatgcgct tgcagcagag gaaaggcaag agtatgacaa taataagact    1140
ggtatttaca caaccacgcc aacaaccctt ggttacccct tccaagcca cttttccgt     1200 ggcacctcat tgttttctgg caaacagttc gccgcaagaa ttcgtaatac tactgacgaa    1260
tgggctgaac gttatgctgc cgataatgct accaatgccg aattgcttaa gaaacagtat    1320
gccatcattg ctagccgtta tgaagaagat tacttgtctc ctattgaaat caacttgact    1380
```

-continued

```
cctgggtatg gtgggacggc tgatgttgac cttacaaata ataaatacca aactgtcaac   1440
cacgtcttga ttgctccttt gtctcgcggt tatactcata tcaaatctgc tgatattgaa   1500
gatgccgtcg atattaatcc tcaatactat tcccacccca tggatgttga tgtccatgtt   1560
gcttctacta aacttgctcg tgaaatcatc tctgcttctc ctggtctcgg tgatatcaat   1620
agtggagaga ctgagcctgg taaggaaatc accagcgata gtgatgttcg caaatggttg   1680
gccgacaatg ttcgctctga ttggcatcct gttggtactt gtgctatgct tcctaaagaa   1740
ttaggtggtg tagttgatcc taacctcaag gtttatggta cttccaactt gcgtgtggtt   1800
gatgcttctg tcatgcctct cgaagtgtct tctcacttga tgcaacccac ttttggtatt   1860
gctgaaaagg ctgctgatat aatcaagtct gccaacaaga agcgaagcaa ctaa         1914
```

<210> SEQ ID NO 3
<211> LENGTH: 593
<212> TYPE: PRT
<213> ORGANISM: Aspergillus oryzae

<400> SEQUENCE: 3

```
Met Leu Phe Ser Leu Ala Phe Leu Ser Ala Leu Ser Leu Ala Thr Ala
1               5                   10                  15

Ser Pro Ala Gly Arg Ala Lys Asn Thr Thr Thr Tyr Asp Tyr Ile Val
                20                  25                  30

Val Gly Gly Gly Thr Ser Gly Leu Val Val Ala Asn Arg Leu Ser Glu
            35                  40                  45

Asn Pro Asp Val Ser Val Leu Leu Leu Glu Ala Gly Ala Ser Val Phe
        50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
    210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285
```

-continued

Ala Lys Lys Glu Val Ile Ile Ser Ala Gly Ala Leu Arg Ser Pro Leu
290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
            325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
            355                 360                 365

Glu Thr Asp Ser Ile Val Ala Ser Leu Arg Ser Gln Leu Ser Asp Tyr
370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
            405                 410                 415

Val Pro Ile Ala Glu Ile Leu Phe His Pro Gly Gly Asn Ala Val
            420                 425                 430

Ser Ser Glu Phe Trp Gly Leu Leu Pro Phe Ala Arg Gly Asn Ile His
            435                 440                 445

Ile Ser Ser Asn Asp Pro Thr Ala Pro Ala Ala Ile Asn Pro Asn Tyr
450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
            485                 490                 495

Glu Thr Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
            515                 520                 525

Val Gly Thr Ala Ala Met Met Pro Arg Ser Ile Gly Gly Val Val Asp
530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
            565                 570                 575

Ala Val Ala Glu Arg Ala Ser Asp Leu Ile Lys Glu Asp Ala Lys Ser
            580                 585                 590

Ala

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ccycargara ayatggghaa ymg                                      23

<210> SEQ ID NO 5
<211> LENGTH: 26
<212> TYPE: DNA
<213> ORGANISM: Artificial Sequence
<220> FEATURE:
<223> OTHER INFORMATION: Primer

```
<400> SEQUENCE: 5
gcrcadgtdc cvacrggrtg ccartc                                              26

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
cgccagggtt ttcccagtca cgac                                                24

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
agcggataac aatttcacac aggaaac                                             27

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
gctactggtg ttgagtggta tcctactgg                                           29

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
gttgccgagt tcttcccaag cgtcaaag                                            28

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
ctggtaagga aatcaccagc gatagtgatg                                          30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
atcttcttca taacggctag caatgatggc                                          30

<210> SEQ ID NO 12
```

```
<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ccttctccac tagcagtttc ctaaatcagc                                    30

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
gctaaataaa atagatggct acaagcttat acttg                              35

<210> SEQ ID NO 14
<211> LENGTH: 32
<212> TYPE: DNA
<213> ORGANISM: Artificial Sequence
<220> FEATURE:
<223> OTHER INFORMATION: Primer

<400> SEQUENCE: 14
taatattctc gatcctgtaa atgcccgtcg tg                                 32

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
ttttatgtag ccagcgtaag catcagcacg acg                                33

<210> SEQ ID NO 16
<211> LENGTH: 637
<212> TYPE: PRT
<213> ORGANISM: Circinella

<400> SEQUENCE: 16
```

Met Lys Ile Ser Ala Ala Val Val Thr Ile Val Thr Ala Phe Ala Ser
1               5                   10                  15

Val Ala Thr Ala Gln Gln Gln Asn Thr Ser Glu Thr Asn Thr Tyr Asp
            20                  25                  30

Tyr Val Ile Val Gly Gly Gly Val Gly Gly Leu Ala Leu Ala Ser Arg
        35                  40                  45

Leu Ser Glu Asn Lys Gly Val Ser Val Ala Val Leu Glu Ala Gly Pro
    50                  55                  60

Tyr Ala Gly Asp Gln Phe Val Tyr Ala Pro Gly Met Tyr Gly Gln
65                  70                  75                  80

Ala Val Gly Thr Asp Leu Cys Pro Leu Leu Pro Thr Thr Pro Gln Glu
                85                  90                  95

Asn Met Gly Asn Arg Ser Leu Ser Ile Ala Thr Gly Lys Leu Leu Gly
            100                 105                 110

Gly Gly Ser Ser Val Asn Gly Leu Val Trp Thr Arg Gly Gly Leu Lys
        115                 120                 125

Asp Phe Asp Ala Trp Glu Glu Leu Gly Asn Pro Gly Trp Asn Gly Ala

```
            130                 135                 140
Ser Met Phe Asn Tyr Phe Lys Val Glu Asn Phe Thr Pro Pro Thr
145                 150                 155                 160

Pro Ala Gln Ala Ala Tyr Gly Ala Thr Tyr Gln Lys Asn Ala His Gly
                165                 170                 175

Thr Lys Gly Pro Met Asp Val Ser Phe Thr Asn Phe Glu Phe Pro Gln
            180                 185                 190

Ser Gly Asn Trp Asn Ala Ser Leu Asn Ala Val Gly Phe Thr Ala Val
                195                 200                 205

Pro Asp Leu Leu Asn Gly Thr Leu His Gly Tyr Ser Thr Thr Pro Asn
210                 215                 220

Ile Leu Asp Pro Val Asn Ala Arg Arg Ala Asp Ala Tyr Ala Gly Tyr
225                 230                 235                 240

Ile Lys Pro Tyr Ile Ser Arg Asn Asn Leu Ala Val Leu Ala Asn His
                245                 250                 255

Thr Val Ser Arg Ile Gln Phe Ala Pro Gln Ser Gly Ser Gln Pro Leu
                260                 265                 270

Arg Ala Thr Gly Val Glu Trp Tyr Pro Thr Gly Asp Lys Ser Gln Lys
            275                 280                 285

Gln Val Leu Asn Ala Arg Tyr Glu Val Ile Leu Ser Ser Gly Ala Ile
            290                 295                 300

Gly Ser Pro Lys Leu Leu Glu Leu Ser Gly Ile Gly Asn Lys Asp Ile
305                 310                 315                 320

Val Ala Ala Ala Gly Ile Gln Ser Leu Leu Asp Leu Pro Gly Val Gly
                325                 330                 335

Ser Asn Met Gln Asp His Val His Ala Val Thr Val Ser Thr Thr Asn
                340                 345                 350

Ile Thr Gly Tyr Thr Thr Asn Ser Ile Phe Thr Asn Asp Ala Leu Ala
            355                 360                 365

Ala Glu Glu Arg Gln Glu Tyr Asp Asn Asn Lys Thr Gly Ile Tyr Thr
370                 375                 380

Thr Thr Pro Asn Asn Leu Gly Tyr Pro Ser Pro Ser Gln Leu Phe Arg
385                 390                 395                 400

Gly Thr Ser Phe Val Ser Gly Lys Gln Phe Ala Ala Arg Ile Arg Asn
                405                 410                 415

Thr Thr Asp Glu Trp Ala Glu Arg Tyr Ala Ala Asp Asn Ala Thr Asn
            420                 425                 430

Ala Glu Leu Leu Lys Lys Gln Tyr Ala Ile Ile Ala Ser Arg Tyr Glu
            435                 440                 445

Glu Asp Tyr Leu Ser Pro Ile Glu Ile Asn Leu Thr Pro Gly Tyr Gly
            450                 455                 460

Gly Thr Ala Asp Val Asp Leu Thr Asn Asn Lys Tyr Gln Thr Val Asn
465                 470                 475                 480

His Val Leu Ile Ala Pro Leu Ser Arg Gly Tyr Thr His Ile Lys Ser
                485                 490                 495

Ala Asp Ile Glu Asp Ala Val Asp Ile Asn Pro Gln Tyr Tyr Ser His
            500                 505                 510

Pro Met Asp Val Asp Val His Ala Ser Thr Lys Leu Ala Arg Glu
            515                 520                 525

Ile Ile Ser Ala Ser Pro Gly Leu Gly Asp Ile Asn Ser Gly Glu Thr
            530                 535                 540

Glu Pro Gly Lys Glu Ile Thr Ser Asp Ser Asp Val Arg Lys Trp Leu
545                 550                 555                 560
```

| Ala | Asp | Asn | Val | Arg | Ser | Asp | Trp | His | Pro | Val | Gly | Thr | Cys | Ala | Met |
|---|---|---|---|---|---|---|---|---|---|---|---|---|---|---|---|
| | | | | 565 | | | | 570 | | | | | 575 | | |

| Leu | Pro | Lys | Glu | Leu | Asp | Gly | Val | Val | Asp | Pro | Asn | Leu | Lys | Val | Tyr |
|---|---|---|---|---|---|---|---|---|---|---|---|---|---|---|---|
| | | | 580 | | | | | 585 | | | | | 590 | | |

| Gly | Thr | Ser | Asn | Leu | Arg | Val | Val | Asp | Ala | Ser | Val | Met | Pro | Leu | Glu |
|---|---|---|---|---|---|---|---|---|---|---|---|---|---|---|---|
| | | | 595 | | | | 600 | | | | | 605 | | | |

| Val | Ser | Ser | His | Leu | Met | Gln | Pro | Thr | Phe | Gly | Ile | Ala | Glu | Lys | Ala |
|---|---|---|---|---|---|---|---|---|---|---|---|---|---|---|---|
| | | 610 | | | | 615 | | | | | 620 | | | | |

| Ala | Asp | Ile | Ile | Lys | Ser | Ala | Asn | Lys | Lys | Arg | Ser | Asn |
|---|---|---|---|---|---|---|---|---|---|---|---|---|
| 625 | | | | | 630 | | | | | 635 | | |

<210> SEQ ID NO 17
<211> LENGTH: 1914
<212> TYPE: DNA
<213> ORGANISM: Circinella

<400> SEQUENCE: 17

```
atgaagatat ctgctgctgt agttactatt gttacagctt tcgcttctgt cgctacggct        60
caacagcaaa ataccagtga aactaatacc tacgactacg ttattgttgg tggtggtgta       120
ggaggtttag ctttggctag tcgtctatct gaaaacaagg gtgtttcagt tgctgtactc       180
gaagcaggtc cgtatgctgg agatcagttt gtagtttacg ctcctggcat gtatggccaa       240
gctgtgggta ctgatctctg tcctctcctt cctactactc ctcaagagaa tatggggaac       300
agaagtctta gtattgccac tggtaaattg ctcggtggcg tagttctgt caatggcctt        360
gtttggacac ggggtggttt aaaagacttt gacgcttggg aagaactcgg caaccctggc       420
tggaacggtg ccagcatgtt caattacttt aaaaaggttg aaaactttac ccctcccact       480
cctgctcaag cagcatatgg tgccacttat caaaagaatg ctcatggcac aaagggtcct       540
atggatgttt cctttacaaa tttcgaattt cctcagtctg caactggaa cgcttctctc        600
aacgctgttg gctttactgc tgtccctgat ctcttaaacg gtacacttca tggttattct       660
actacaccta atattctcga tcctgtaaat gcccgtcgtg ctgatgctta cgctggctac       720
ataaaaccct acataagccg taataacctc gctgtcttgg ctaaccatac tgttttcacgt       780
attcaatttg ctccccaaag tggtagccaa cctcttcgcg ctactggtgt tgagtggtat        840
cctactggtg acaaatctca aaagcaagtc ttgaatgctc gctatgaagt tattctctcg       900
tctggtgcta ttggtagccc caagcttttg gagctgtctg gtattggtaa caaggacatt       960
gtcgctgccg ctggtattca atctttgctt gatttgcctg gtgttggttc taatatgcaa      1020
gatcacgtac atgccgttac ggtttctacc acaaacatca ctggttacac caccaacagc      1080
atctttacca acgatgcgct tgcagcagag gaaaggcaag agtatgacaa taataagact      1140
ggtatttaca caaccacgcc caacaacctt ggttacccct ctccaagcca acttttccgt      1200
ggcacctcat tgtttctgg caaacagttc gccgcaagaa ttcgtaatac tactgacgaa       1260
tgggctgaac gttatgctgc cgataatgct accaatgccg aattgcttaa gaaacagtat      1320
gccatcattg ctagccgtta tgaagaagat tacttgtctc ctattgaaat caacttgact      1380
cctgggtatg gtggtacggc tgatgttgac cttacaaata taaataccaa actgtcaac       1440
cacgtcttga ttgctccttt gtctcgcggt tatactcata tcaaatctgc tgatattgaa      1500
gatgccgtcg atattaatcc tcaatactat tcccaccca tggatgttga tgtccatgtt       1560
gcttctacta aacttgctcg tgaaatcatc tctgcttctc ctggtctcgg tgatatcaat      1620
agtggagaga ctgagcctgg taaggaaatc accagcgata gtgatgttcg caaatggttg      1680
```

```
gccgacaatg ttcgctctga ttggcatcct gttggtactt gtgctatgct tcctaaagaa      1740
ttagatggtg tagttgatcc taacctcaag gtttatggta cttccaactt gcgtgtggtt      1800
gatgcttctg tcatgcctct cgaagtgtct tctcacttga tgcaacccac ttttggtatt      1860
gctgaaaagg ctgctgatat aatcaagtct gccaacaaga agcgaagcaa ctaa            1914

<210> SEQ ID NO 18
<211> LENGTH: 49
<212> TYPE: DNA
<213> ORGANISM: artificial sequence
<220> FEATURE:
<223> OTHER INFORMATION: Primer

<400> SEQUENCE: 18
aaccaaggat ccaaaaaaat gtctatatct gctgctgtag ttactattg                  49

<210> SEQ ID NO 19
<211> LENGTH: 49
<212> TYPE: DNA
<213> ORGANISM: Artificial sequence
<220> FEATURE:
<223> OTHER INFORMATION: Primer

<400> SEQUENCE: 19
agagagggat ccctcgagtt agttgcttcg cttcttgttg gcagacttg                  49
```